US010173037B2

(12) United States Patent
Ishida

(10) Patent No.: US 10,173,037 B2
(45) Date of Patent: Jan. 8, 2019

(54) CATHETER ASSEMBLY

(71) Applicant: TERUMO KABUSHIKI KAISHA, Shibuya-ku, Tokyo (JP)

(72) Inventor: Masahiro Ishida, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 207 days.

(21) Appl. No.: 15/220,791

(22) Filed: Jul. 27, 2016

(65) Prior Publication Data

US 2016/0331940 A1 Nov. 17, 2016

Related U.S. Application Data

(63) Continuation of application No. PCT/JP2015/051777, filed on Jan. 23, 2015.

(30) Foreign Application Priority Data

Jan. 29, 2014 (JP) ................................ 2014-014123

(51) Int. Cl.
A61M 25/06 (2006.01)
A61M 5/158 (2006.01)
A61M 39/06 (2006.01)

(52) U.S. Cl.
CPC ........ *A61M 25/0631* (2013.01); *A61M 5/158* (2013.01); *A61M 25/0606* (2013.01); *A61M 39/0606* (2013.01); A61M 25/0693 (2013.01); A61M 2039/062 (2013.01)

(58) Field of Classification Search
CPC .......... A61M 25/0631; A61M 25/0606; A61M 5/158; A61M 2039/062
See application file for complete search history.

(56) References Cited

U.S. PATENT DOCUMENTS

2004/0044313 A1 3/2004 Nakajima
2011/0282285 A1* 11/2011 Blanchard ......... A61M 25/0097
604/164.08

FOREIGN PATENT DOCUMENTS

| JP | 2004-528952 A | 9/2004 |
|---|---|---|
| JP | 3808806 B2 | 8/2006 |
| JP | 2013-529111 A | 7/2013 |
| WO | WO 02/102442 A1 | 12/2002 |
| WO | 2011/143621 A1 | 11/2011 |

(Continued)

OTHER PUBLICATIONS

International Search Report (PCT/ISA/210) dated Apr. 21, 2015, by the Japanese Patent Office as the International Searching Authority for International Application No. PCT/JP2015/051777.

(Continued)

*Primary Examiner* — Bradley J Osinski
(74) *Attorney, Agent, or Firm* — Buchanan Ingersoll & Rooney PC

(57) ABSTRACT

A catheter assembly is disclosed, which includes a catheter, a catheter hub coupled to the catheter, an inner needle having a needlepoint, a housing coupled to the inner needle, and a protector that covers at least the needlepoint of the inner needle in accordance with evulsion of the inner needle from the catheter. In an initial state, the catheter and the inner needle are exposed from a leading end of the housing, and the catheter hub and the protector are housed in the housing.

18 Claims, 27 Drawing Sheets

(56) References Cited

FOREIGN PATENT DOCUMENTS

WO     WO 2011/143621 A1    11/2011
WO     WO 2013/172104 A1    11/2013

OTHER PUBLICATIONS

Written Opinion (PCT/ISA/237) dated Apr. 21, 2015, by the Japanese Patent Office as the International Searching Authority for International Application No. PCT/JP2015/051777.
Notification of Reasons for Refusal dated Aug. 14, 2018, in corresponding Japanese Application No. 2015-559906, and an English language machine translation thereof.

* cited by examiner

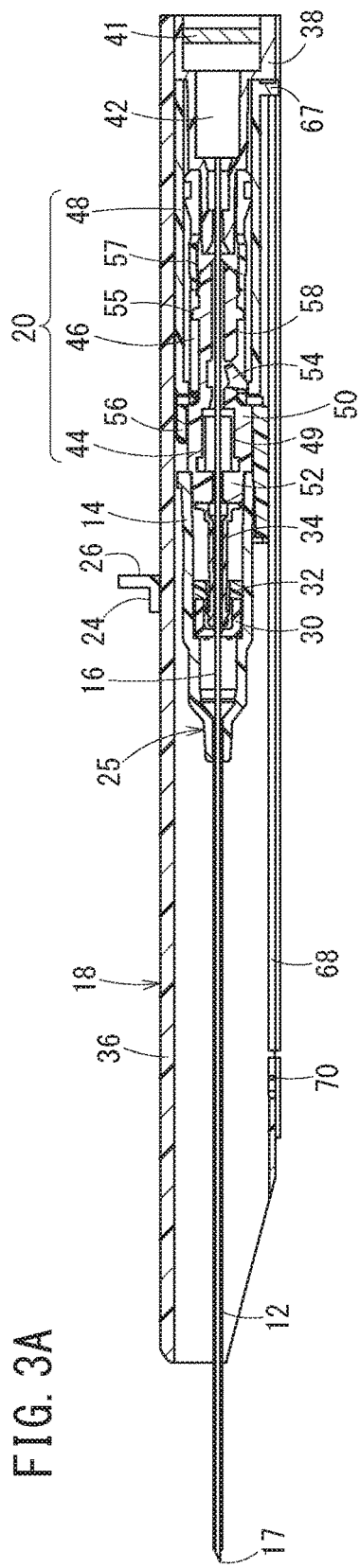
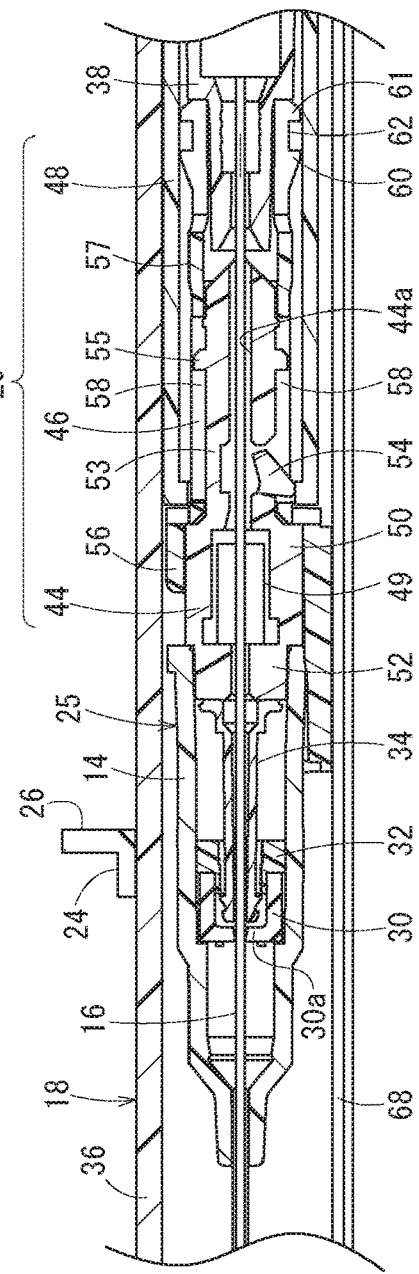
FIG. 3A
FIG. 3B

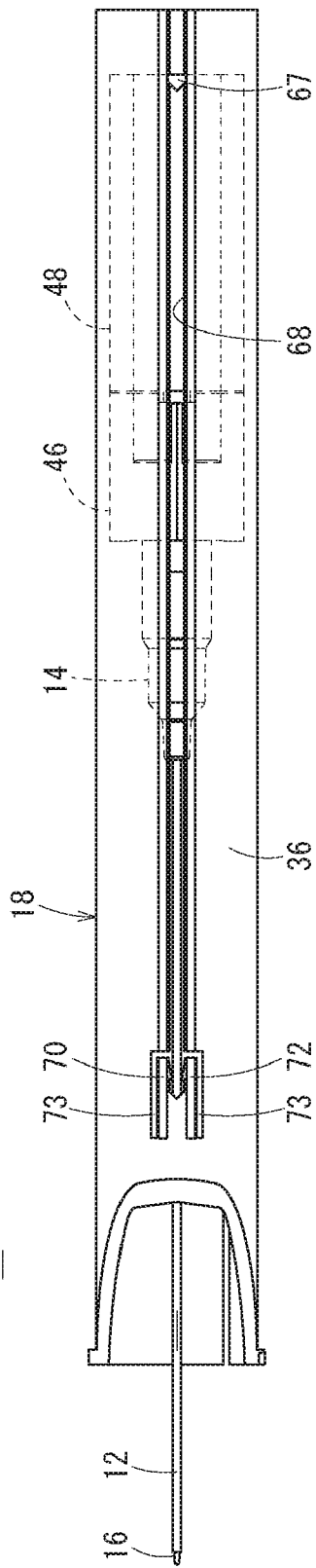
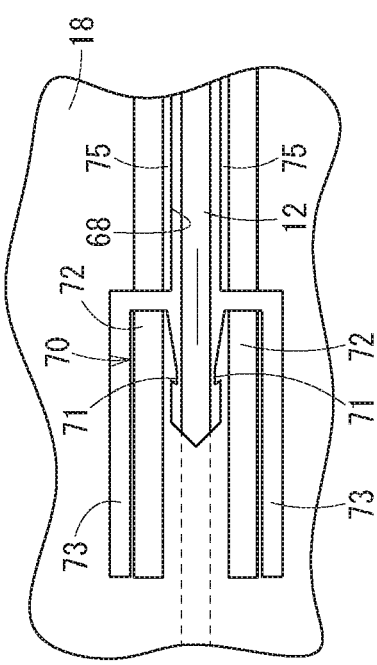
FIG. 5A
FIG. 5B

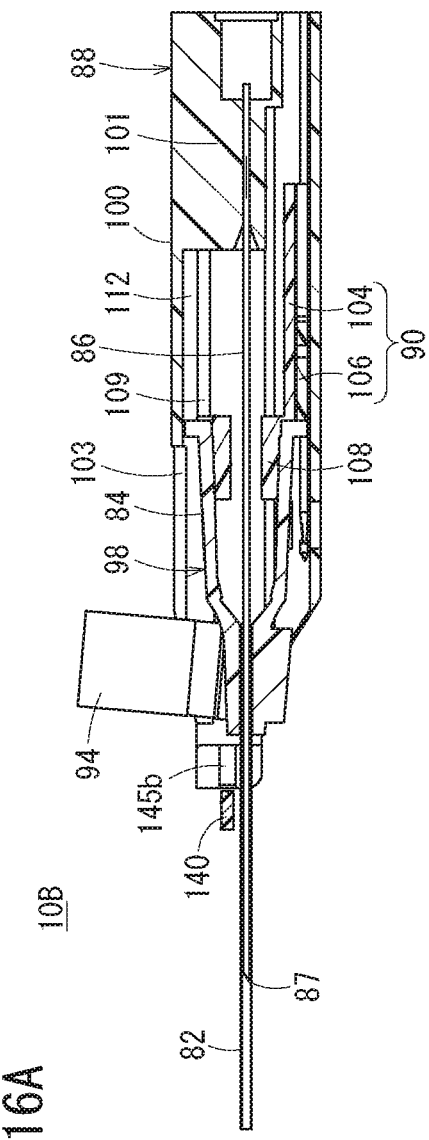
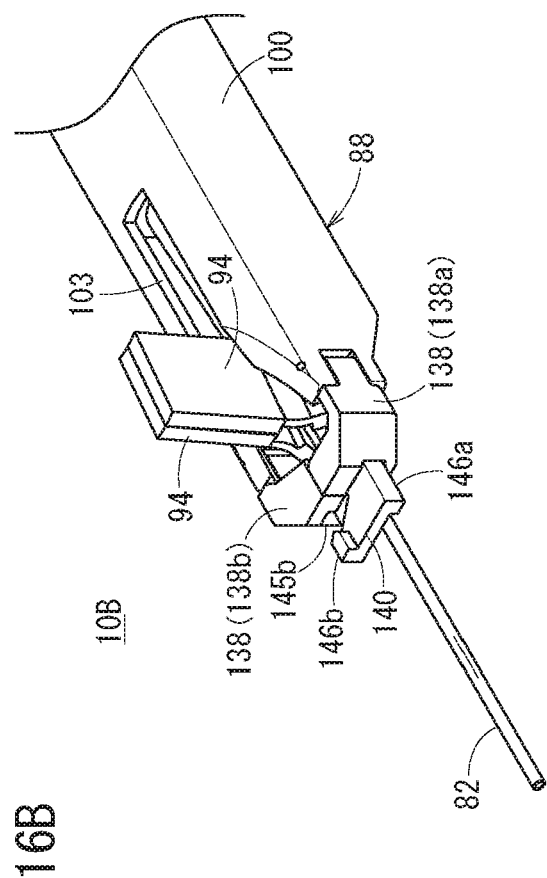
FIG. 16A
FIG. 16B

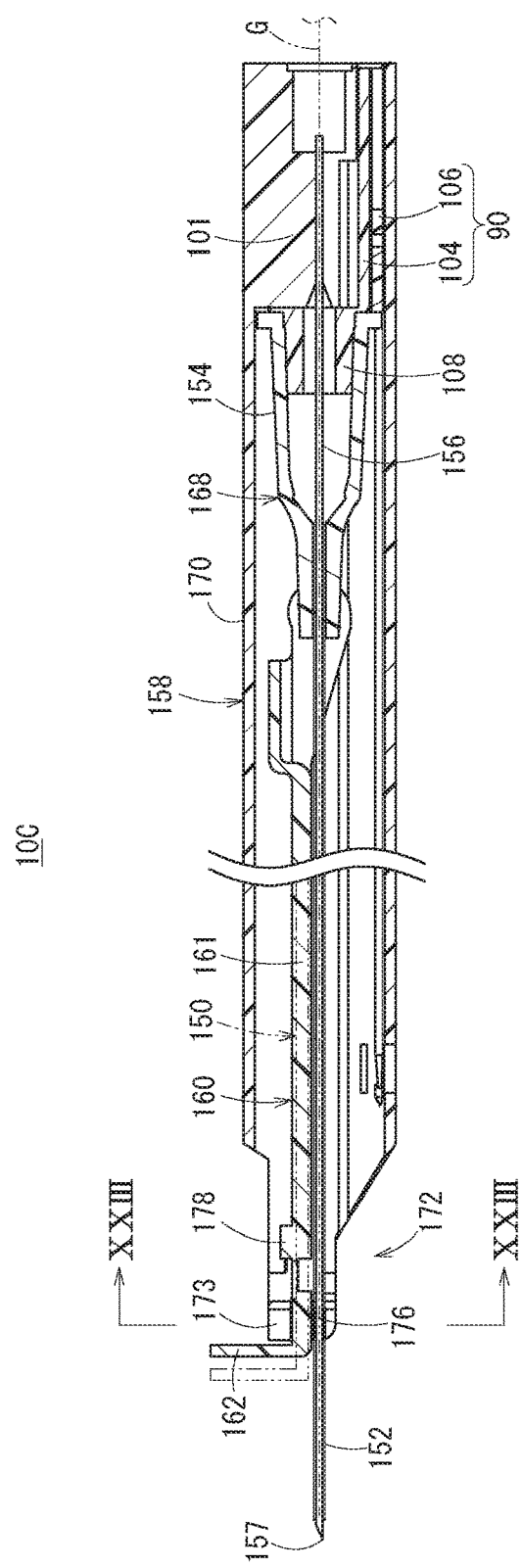

CATHETER ASSEMBLY

CROSS-REFERENCES TO RELATED APPLICATIONS

This application is a continuation of International Application No. PCT/JP2015/051777 filed on Jan. 23, 2015, which claims priority to JP 2014-014123 filed on Jan. 29, 2014, the entire content of which are incorporated herein by reference.

TECHNICAL FIELD

The present disclosure relates to a catheter assembly that punctures a blood vessel and can be, for example, detained upon performing a transfusion to a patient.

BACKGROUND DISCUSSION

Conventionally, when a transfusion is performed to a patient, for example, a catheter assembly is used. The catheter assembly can include a hollow catheter, a catheter hub adhered to a base end of the catheter, an inner needle inserted into the catheter and having a sharp needlepoint at a leading end, and a needle hub adhered to a base end of the inner needle. In a case where a transfusion is performed to a patient by using the catheter assembly, the catheter with the inner needle punctures a blood vessel of the patient, and the inner needle is evulsed from the catheter while the catheter is puncturing the patient after the puncture. Next, a connector provided at an end portion of a transfusion tube is coupled to a base end of the catheter hub, and a transfusion material is supplied into the blood vessel of the patient through the transfusion tube, the catheter hub, and the catheter.

In the use of the above catheter assembly, in order to help prevent a user from carelessly touching an inner needle having a sharp needlepoint after the inner needle has been evulsed from a catheter, a catheter assembly including a protector, capable of covering the inner needle after the evulsion has been proposed (for example, refer to JP 3808806 B1).

In a case of the conventional catheter assembly including a protector, a needle hub is constituted as a housing. In an initial state (before use), a leading end of the housing can include a base end of a catheter hub positioned thereat, and an exposure length of the inner needle from the housing is long. When a protecting function of the protector appears, a state where the protector that has been housed in the housing protrudes from the leading end of the housing and covers the inner needle protruding from the housing with the needlepoint, is acquired. Due to the above configuration, the conventional catheter assembly including a protector has a long entire product length in both the initial state and the needlepoint protecting state.

SUMMARY

It would be desirable to have a catheter assembly having a shorter entire product length, and which can have excellent storage before use and can be relatively easy to use due to its compactness. In addition, waste after use is relatively compact, and waste disposal can be performed relatively easily.

A catheter assembly is disclosed capable of shortening an entire product length in comparison to a conventional catheter assembly including a protector.

A catheter is disclosed, which includes a catheter hub fixed to a base end portion of the catheter; an inner needle having a needlepoint, and inserted into the catheter so as to be separable; a housing coupled to the inner needle; and a protector displaceable in an axial direction in a range regulated with respect to the housing, and configured to cover at least the needlepoint of the inner needle in accordance with evulsion of the inner needle from the catheter. In an initial state, the catheter and the inner needle are exposed from a leading end of the housing, and the catheter hub and the protector are housed in the housing.

With the above configuration, since the catheter hub has been housed in the housing, an exposure length of the inner needle from the housing can be shortened in comparison to the conventional technique. Accordingly, an entire length of the catheter assembly in the initial state, namely, a length from a base end of the housing to a leading end of the inner needle can be made shorter than that of the conventional catheter assembly. Accordingly, excellent storage due to its compactness is acquired and a puncture operation is easily performed. Since the exposure length of the inner needle from the housing is short, the protector may be also made to be short. Accordingly, an entire product length even in a state where the protector has covered the needlepoint (a protecting function appearance state) is short. Therefore, a waste is compact, and disposal is relatively easy to perform.

According to an exemplary embodiment, the above catheter assembly may further include a locking mechanism preventing displacement of the protector with respect to the housing in a state where the protector has covered the needlepoint. A passage formed of a groove or a hole extending in the axial direction, may be provided on a wall portion included in the housing. The locking mechanism may have an engaging portion protruding in the passage, and an engaging protrusion provided to the protector and capable of engaging with the engaging portion. With this configuration, there is no need for a structure protruding inward in the housing in order to engage the housing and the protector. Thus, a forward movement of the catheter hub in the housing is not hindered. Accordingly, a forward movement operation of the catheter can be smoothly performed.

According to an exemplary embodiment of the above catheter assembly, a coming-off prevention protrusion for preventing the engaging protrusion from coming off into the housing may be provided on the engaging protrusion. With this configuration, even in a case where the housing is deflected, engagement between the engaging portion and the engaging protrusion is prevented from being released.

According to an exemplary embodiment of the above catheter assembly, an operating portion for operating the catheter hub may be provided on the catheter hub, and in the initial state, at least a part of the operating portion may be exposed from the housing. With this configuration, the operating portion exposed from the housing is touched so that the catheter hub can be operated. Thus, a forward movement operation of the catheter can be performed relatively easily.

According to an exemplary embodiment of the above catheter assembly, a slit extending in the axial direction and open on a leading end side of the housing may be provided on the housing, and at least the part of the operating portion may be exposed on an outside of the housing through the slit. With this configuration, the operating portion can be exposed on the outside of the housing with a relatively simple structure.

According to an exemplary embodiment of the above catheter assembly, the slit may be provided so as to be shifted to one side in a left and right direction with respect to a center of the housing. With this configuration, when a puncture is operated, the inner needle can be prevented from being exposed outside the housing through the slit.

According to an exemplary embodiment of the above catheter assembly, the operating portion may have a tab exposed outside the housing, and a coupling portion coupling the tab and the catheter hub, and the coupling portion may have flexibility in order to allow the operating portion to fall to a side of the catheter hub. With this configuration, upon using a dressing material in order to fix the catheter hub to skin of a patient, when the operating portion falls to the side of the catheter hub, it is easy to stick the dressing material without making the operating portion an obstacle.

According to an exemplary embodiment of the above catheter assembly, the coupling portion may have a pedestal configured to abut on an outer surface of the housing so as to be slidable, and the tab may be provided on the pedestal. With this configuration, upon performing a forward movement operation of the catheter hub, the housing supports the pedestal. Thus, deflection in the axial direction of the coupling portion can be inhibited or prevented, and a relatively stable operation can be performed.

According to an exemplary embodiment of the above catheter assembly, the operating portion may include a pair of wings mutually protruding in opposite directions from the catheter hub and having flexibility, and the pair of wings may be folded, overlapped each other, and may protrude from the slit in the initial state, and may be expansible in a state of separation from the slit. With this configuration, since the pair of wings functions as the operating portion in the initial state, there is no need for providing an exclusive operating portion to the catheter hub. Thus, a configuration can be simplified.

According to an exemplary embodiment of the above catheter assembly, in the initial state, the operating portion may extend along the inner needle and the catheter hub, a base end portion may be coupled to the catheter hub, and a leading end portion may be exposed on a leading end side of the housing. With this configuration, a portion of the operating portion that has been exposed on the leading end side of the housing is touched so that an operation with respect to the operating portion can be performed. Thus, the same hand that grips the leading end side of the housing upon a puncture can operate the operating portion. Accordingly, between upon a puncture and upon a forward movement operation of the catheter, there is no need for shifting a hand that performs the operation. Thus, excellent operability can be acquired.

According to an exemplary embodiment, the above catheter assembly may further include a needle support portion configured to support the inner needle through the catheter on a leading end side beyond the catheter hub. The needle support portion may be provided movable with respect to the housing in order to change from a first state of supporting the inner needle to a second state of releasing the support of the inner needle and allowing the catheter hub to pass. With this configuration, deflection of the inner needle upon a puncture is inhibited or prevented, and a relatively stable puncture can be performed.

According to an exemplary embodiment of the above catheter assembly, the needle support portion may have a pair of support arms openable and closeable, and a restraining portion capable of restraining the pair of support arms in a closed state and releasing the restraint. With this configuration, the pair of support arms can securely support the inner needle upon a puncture. In addition, upon a forward movement of the catheter hub, the pair of support arms opens so that the movement of the catheter hub with respect to the housing can be securely allowed.

A catheter assembly is disclosed comprising: a catheter; a catheter hub fixed to a base end portion of the catheter; an inner needle having a needlepoint, and inserted into the catheter so as to be separable; a housing coupled to the inner needle; and a protector displaceable in an axial direction in a range regulated with respect to the housing, and configured to cover at least the needlepoint of the inner needle in accordance with evulsion of the inner needle from the catheter.

According to the catheter assembly of the present disclosure, the entire product length can be shortened in comparison to the conventional catheter assembly including a protector.

BRIEF DESCRIPTION OF THE DRAWINGS

FIG. 3A is a longitudinal-sectional view of the catheter assembly illustrated in FIG. 1.

FIG. 3B is a partially enlarged view of FIG. 3A.

FIG. 5A is a bottom view of the catheter assembly in an initial state.

FIG. 5B is a partially enlarged view of FIG. 5A.

FIG. 7 is a longitudinal-sectional view of the catheter assembly illustrated in FIG. 1 in a state where a protector has extended partway through.

FIG. 8 is a perspective view of the catheter assembly illustrated in FIG. 1 in the state where a protector has extended partway through.

FIG. 16A is a longitudinal-sectional view of the catheter assembly illustrated in FIG. 11 in a state where a catheter hub has moved forward partway through.

FIG. 16B is a perspective view of the catheter assembly illustrated in FIG. 11 in the state where a catheter hub has moved forward partway through.

FIG. 21 is a partially omitted longitudinal-sectional view of the catheter assembly illustrated in FIG. 19.

DETAILED DESCRIPTION

Preferred embodiments regarding a catheter assembly according to the present disclosure, will be given and described below with reference to the drawings.

Figure 1:
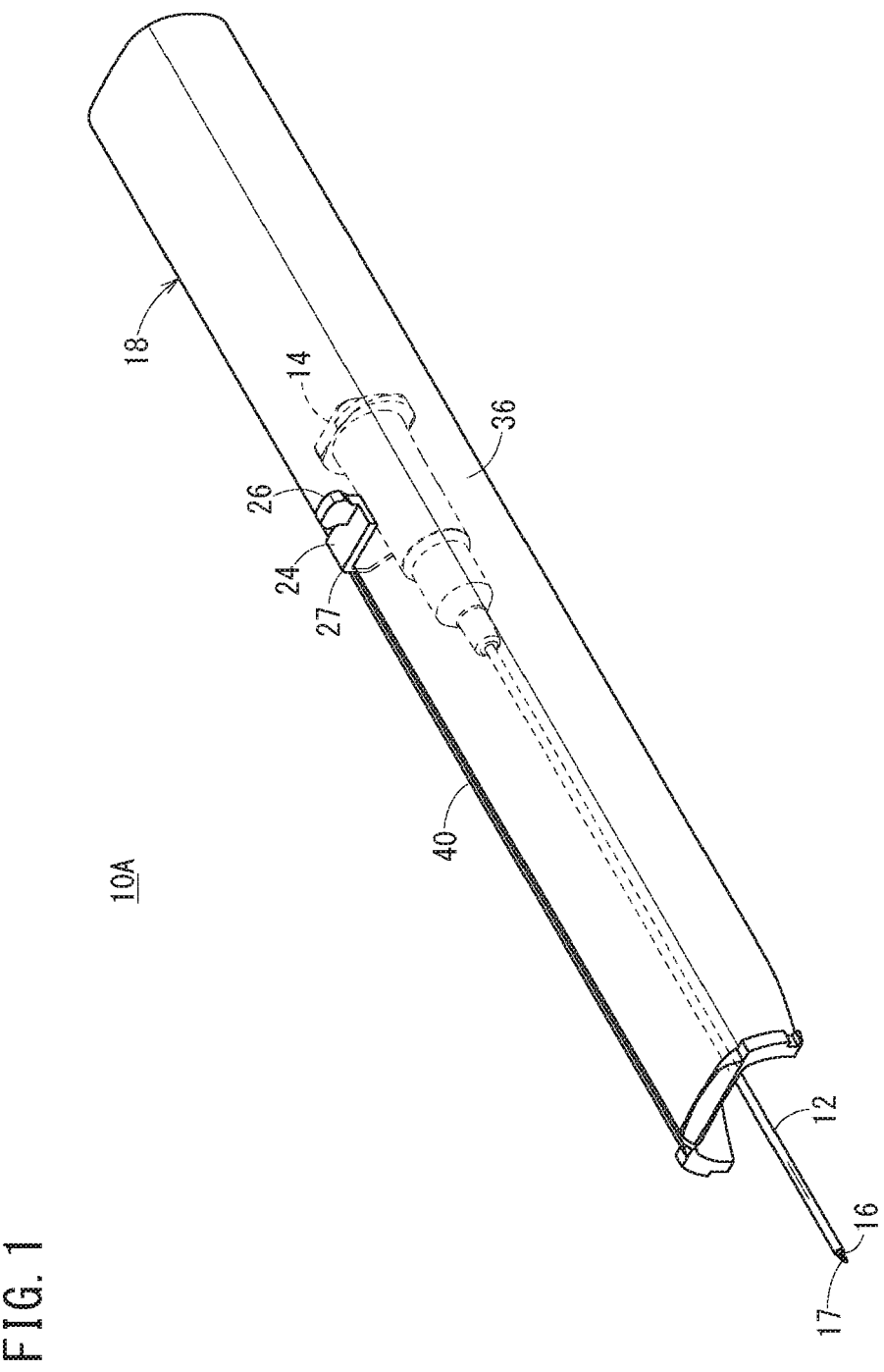
FIG. 1 is a perspective view of a catheter assembly according to a first embodiment of the present disclosure.
Figure 2:
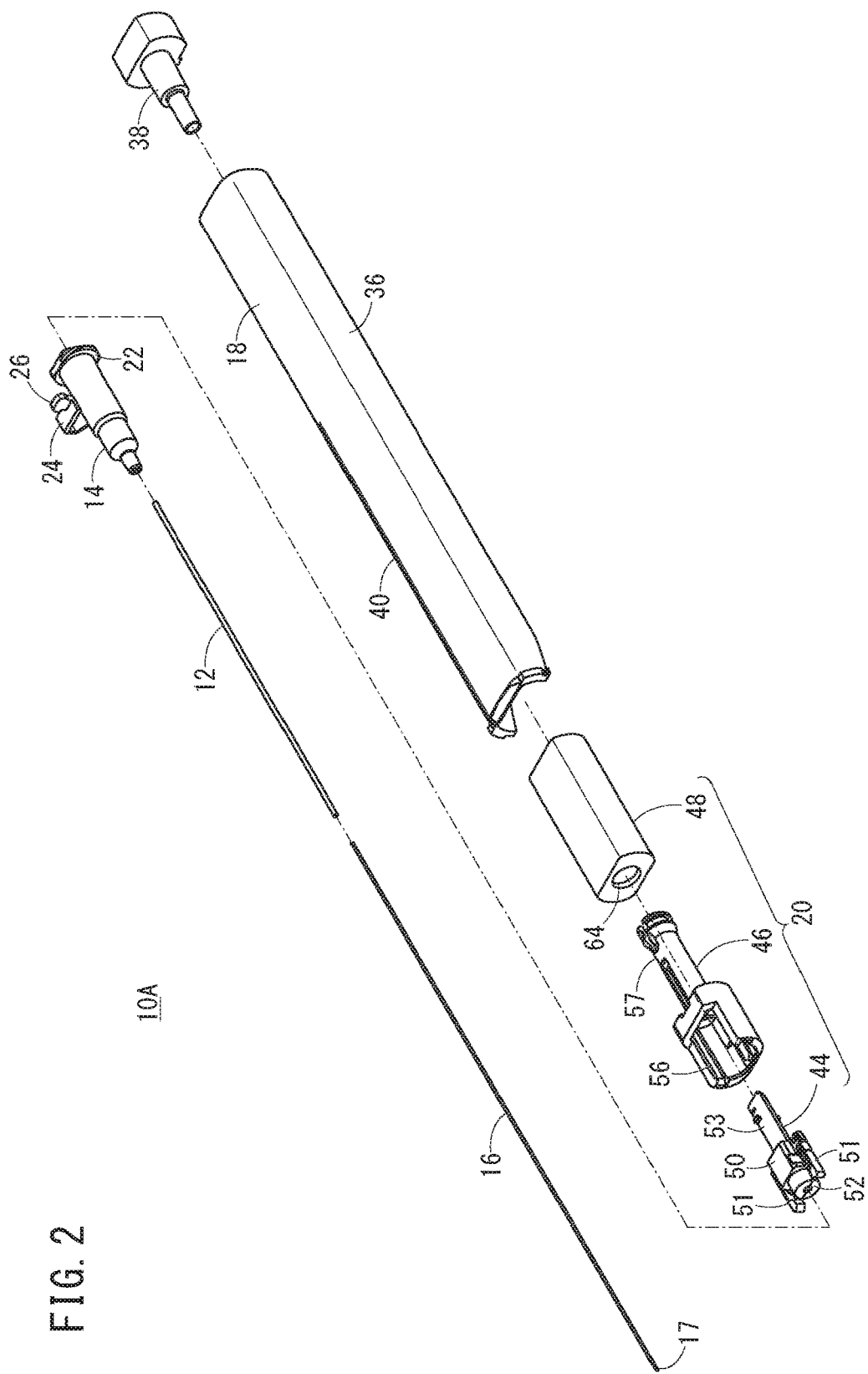
FIG. 2 is an exploded perspective view of the catheter assembly illustrated in FIG. 1.

FIG. 1 is a perspective view of a catheter assembly 10A according to a first embodiment of the present disclosure. FIG. 2 is an exploded perspective view of the catheter assembly 10A. FIG. 3A is a longitudinal-sectional view of the catheter assembly 10A. FIG. 3B is a partially enlarged view of FIG. 3A.

The catheter assembly 10A can include a tubular catheter 12 functioning as an outer needle, a catheter hub 14 coupled to the side of a base end of the catheter 12, a tubular inner needle 16 having a sharp needlepoint 17 on a leading end and insertable into the inside of the catheter 12, a housing 18 coupled to the inner needle 16 and serving as a needle hub, and a protector 20 that covers the needlepoint 17 of the inner needle 16 upon evulsion of the inner needle 16.

With the catheter assembly 10A, a user (for example, a medical doctor or a nurse) grips and operates the housing 18 so that a leading end portion of the housing 18 can puncture a blood vessel of a patient. The catheter assembly 10A has a double tubular structure in which the inner needle 16 has been inserted into the catheter 12 and the inner needle 16 has protruded from a leading end of the catheter 12 by a predetermined length in an initial state before use (before a puncture to the patient). In the initial state of the catheter assembly 10A, the catheter hub 14 and the housing 18 have been coupled through the protector 20.

The catheter assembly 10A in the initial state can include one assembly having the double tubular structure of the catheter 12 and the inner needle 16, the catheter hub 14, the protector 20, and the housing 18 combined, and is integrally operable.

The catheter 12 is a tubular member that has been formed so as to have a predetermined length, with a small diameter and flexibility. A resin material and, in particular, a soft resin material are preferable as examples of a constituent material of the catheter 12. In this case, for example, the material of the catheter 12, can include fluororesins, such as polytetrafluoroethylene (PTFE), ethylene-tetrafluoroethylene copolymer (ETFE), and perfluoroalkoxy fluoropolymer (PFA), olefin resins, such as polyethylene and polypropylene, or a mixture thereof, polyurethane, polyester, polyamide, polyether nylon resin, and a mixture of the olefin resin and ethylene-vinyl acetate copolymer. The catheter 12 may include a resin having transparency so that the entire or partial inside can be visually ascertained.

The catheter hub 14 is coupled and fixed to the base end of the catheter 12. A flange portion 22 protruding outward, extending in a circumferential direction, and serving as a male screw, is provided on a base end of the catheter hub 14.

The catheter hub 14 is provided with a hub operating portion 24 for operating the catheter hub 14. The hub operating portion 24 has been integrally formed with respect to the catheter hub 14. The hub operating portion 24 may be constituted as a component separated from the catheter hub 14, and may be attachable to and detachable from the catheter hub 14

As illustrated in FIG. 1, in the initial state, at least a part of the hub operating portion 24 is exposed from the housing 18. The hub operating portion 24 can include a tab 26 exposed outside the housing 18, and a coupling portion 27 coupling the tab 26 and the catheter hub 14. The tab 26 protrudes upward from the coupling portion 27. The user touches and grips or presses the tab 26 so that the catheter hub 14 can be operated in an axial direction.

Figure 4A:
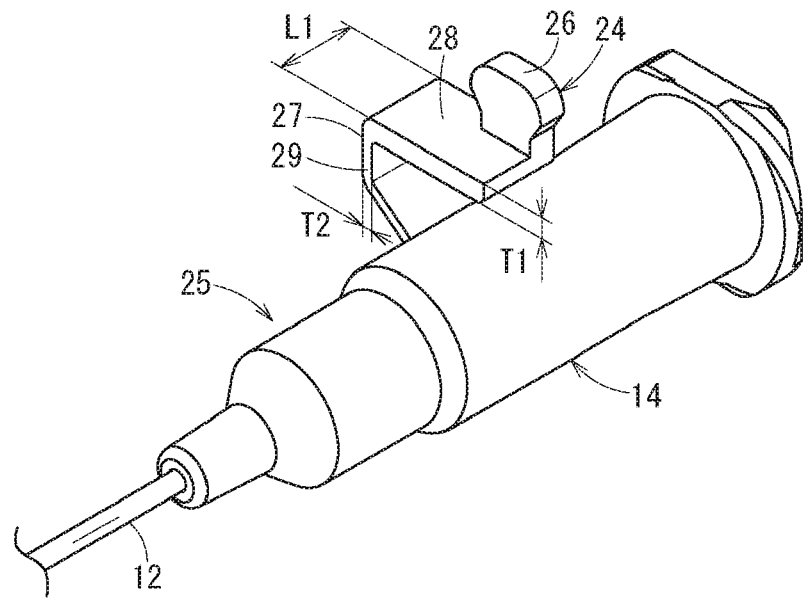
FIG. 4A is a perspective view of a catheter hub and a hub operating portion (an initial shape).

As illustrated in FIG. 4A, the coupling portion 27 has a pedestal 28 on which the tab 26 is provided, and a thin-walled portion 29 provided between the pedestal 28 and the catheter hub 14. The coupling portion 27 has a shape that bends so as to be lateral, substantially U-shaped as a whole in a natural state in which no external force acts (FIG. 4A). The pedestal 28 abuts on an outer surface of the housing 18 (an upper surface in FIG. 1) and is slidable in an axial direction of the housing 18.

Figure 4B:
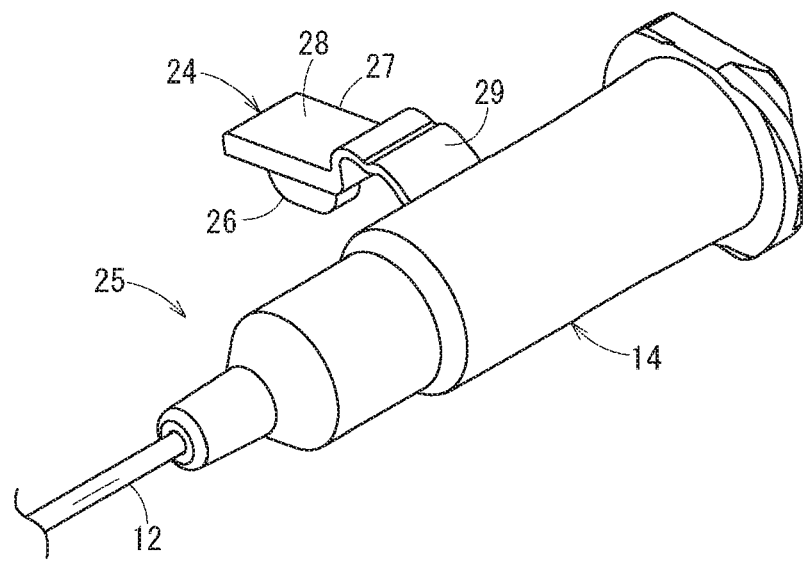
FIG. 4B is a perspective view of the catheter hub and the hub operating portion (a shape upon transformation).

A thickness T2 of the thin-walled portion 29 is thinner than a thickness T1 of the pedestal 28. A length L1 in an axial direction of the coupling portion 27 is larger than the thickness T2 of the thin-walled portion 29. Accordingly, the coupling portion 27 barely deforms in an axial direction of the catheter hub 14, but easily deforms at a part of the thin-walled portion 29 in a direction perpendicular to the axial direction. As illustrated in FIG. 4B, the coupling portion 27 has flexibility so that the hub operating portion 24 falls to the side of the catheter hub 14.

Hereinafter, a member including the catheter 12, the catheter hub 14, and the hub operating portion 24, will be referred to as a "catheter member 25".

Upon the use of the catheter assembly 10A, the catheter hub 14 is exposed on skin of the patient, stuck, and detained on the skin with a dressing material or a tape in a state where the catheter 12 has punctured the blood vessel. The above catheter hub 14 preferably can include a material harder than the catheter 12. Examples of the constituent material of the catheter hub 14 that can be preferably used include, but are not particularly limited to, thermoplastic resins, such as polypropylene, polycarbonate, polyamide, polysulfone, polyarylate, and methacrylate-butylene-styrene copolymer.

As illustrated in FIG. 3B, according to the present embodiment, a hemostasis valve 30 having a valve portion 30a including a slit formed thereon, a seal member 32 disposed on the side of a base end of the hemostasis valve 30, and a tubular plug 34 capable of passing through the valve portion 30a of the hemostasis valve 30 in accordance with a movement in a leading end direction, are disposed inside the catheter hub 14. A gap through which air can pass is formed between the hemostasis valve 30 and an inner circumferential surface of the catheter hub 14. The seal member 32 is an annular member including a material that allows gas to pass therethrough and help prevent liquid from passing therethrough (for example, a porous body).

When blood flows into the catheter hub 14 through an intra-cavity of the catheter 12 in accordance with the puncture of the catheter 12 to the blood vessel, air that has been present on the leading end side in the catheter hub 14 passes through the seal member 32 and then discharges to the base end side in the catheter hub 14. However, the hemostasis valve 30 and the seal member 32 can prevent the blood from flowing to the base end side of the catheter hub 14.

A leading end of the plug 34 is positioned on the base end side beyond the valve portion 30a of the hemostasis valve 30 and the slit of the valve portion 30a is closed at an initial position illustrated in FIG. 3B (a position before a connector of a transfusion tube is coupled). When the plug 34 moves in the leading end direction in accordance with coupling between the catheter hub 14 and the connector of the transfusion tube, the plug 34 passes through the valve portion 30a of the hemostasis valve 30 so that the leading end side and the base end side of the intra-cavity of the catheter hub 14 communicate with each other. Accordingly, a state where a transfusion can be supplied from a transfusion line to the blood vessel through the catheter member 25 is formed.

The inner needle 16 is a tubular member having rigidity capable of puncturing the skin of the patient in FIGS. 1 and 2. In accordance with an exemplary embodiment, the inner needle 16 is formed sufficiently longer than the catheter 12. In the initial state of the catheter assembly 10A, the needlepoint 17 protrudes from a leading end opening of the catheter 12 by a predetermined length. In addition, in the initial state, the inner needle 16 has a midway part in the longitudinal direction inserted into the inside of the catheter hub 14, and has the side of the base end held inside the housing 18.

Examples of a constituent material of the inner needle 16 can include, for example, metal materials, such as stainless steel, aluminum or an aluminum alloy, titanium or a titanium alloy.

The housing 18 can include a hollow housing main body 36 included in a shell to be gripped by the user, and a hollow inner needle holding member 38 to be fit into the inside on the base end side of the housing main body 36. The housing main body 36 is a cylindrical member that has a hollow portion including predetermined capacity and is formed so as to be slender. The housing main body 36 is formed so as to be appropriate in size (thickness, length) in order to be easily gripped and operated by the user upon the use of the catheter assembly 10A.

In the initial state of the catheter assembly 10A, the catheter 12 and the inner needle 16 are exposed from the leading end of the housing 18, and the catheter hub 14 and the protector 20 are housed in the housing 18. As a result, the leading end of the housing 18 extends to a midway of the catheter 12. According to the present embodiment, a position of the base end of the catheter hub 14 is positioned on the base end side beyond a position of the center in the axial direction of the housing 18, and the leading end of the housing 18 is positioned on the leading end side beyond a position of the center in a longitudinal direction of the catheter 12.

As illustrated in FIGS. 1 and 2, the housing main body 36 can include a slit 40 extending in the axial direction of the housing 18 and open on the leading end side of the housing 18, formed thereon. In the initial state of the catheter assembly 10A, the part of the hub operating portion 24 (the pedestal 28 and the tab 26 in the illustrated example) is exposed outside the housing 18 through the slit 40. The slit 40 is provided so as to be shifted to one side in a left and right direction with respect to the center in the left and right direction of the housing 18. Accordingly, in plan view, the slit 40 and the inner needle 16 are mutually shifted in the left and right direction, and the housing 18 covers right above the inner needle 16.

As illustrated in FIG. 3A, the inner needle holding member 38 is fit and fixed to the base end side of the housing main body 36, and fixes and holds a base end portion of the inner needle 16. A filter 41 capable of preventing liquid and allowing gas to pass therethrough is disposed on the inside of a portion on the base end side of the inner needle holding member 38. A flashback chamber 42 is formed ahead of the filter 41. When the inner needle 16 and the catheter 12 puncture the patient, the blood flows into the flashback chamber 42 through the inner needle 16. The user can determine whether the puncture of the inner needle 16 and the catheter 12 has been appropriately performed, due to the flow of the blood into the flashback chamber 42.

Figure 9:
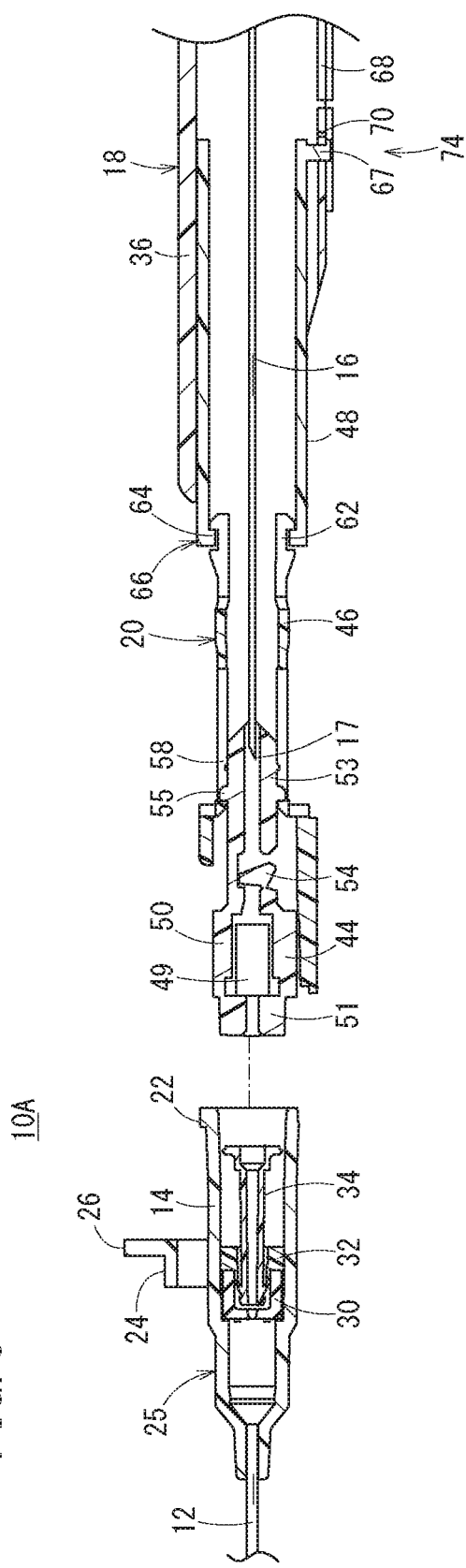
FIG. 9 is a longitudinal-sectional view of the catheter assembly illustrated in FIG. 1 in a state where the catheter hub and the protector have separated from each other.

The protector 20 houses the inner needle 16 so as to cover the needlepoint 17 of the inner needle 16 upon evulsion of the inner needle 16 from the catheter 12. As illustrated in FIGS. 2 and 3B, the protector 20 has an inner tube 44 that fits to the base end of the catheter hub 14 so as to be releasable, an outer tube 46 that can include the inner tube 44 disposed inside and is relatively displaceable in the axis line direction in a range regulated with respect to the inner tube 44, and a nipple 48 that can include the outer tube 46 inserted into the inside and is slidable in the axial direction with respect to the outer tube 46. Upon an evulsion operation of the inner needle 16 from the catheter 12, the protector 20 extends so as to cover an entire length of the inner needle 16 (refer to FIG. 9).

The inner tube 44 functions to cover the needlepoint 17 of the inner needle 16 in accordance with the evulsion of the inner needle 16 from the catheter 12. The inner tube 44 has a shutter housing portion 50 housing a shutter member 49 (refer to FIG. 3B), arms 51 integrally provided on both of the left and right sides of the shutter housing portion 50 (refer to FIG. 2), a leading end cylindrical portion 52 protruding from the shutter housing portion 50 to the leading end side, and a base end cylindrical portion 53 protruding from the shutter housing portion 50 to the base end side. The inner tube 44 can include an insertion hole 44a that passes through in the axial direction and into which the inner needle 16 can be inserted inside (refer to FIG. 3B).

The shutter member 49 is an elastic member formed by bending a plate-like member to be V-shaped. In a state where an apex has faced the side of a leading end of the inner tube 44, the shutter member 49 is disposed in the shutter housing portion 50. In the initial state of the catheter assembly 10A, the shutter member 49 is elastically compressed and deformed by pressure from a side surface of the inner needle 16 so as to be in a compact and closed state.

As illustrated in FIG. 2, the leading end cylindrical portion 52 is cylindrical. In a state where the catheter hub 14 and the inner tube 44 have engaged (coupled) with each other, the leading end cylindrical portion 52 fits into the base end of the catheter hub 14. A hollow portion of the leading end cylindrical portion 52 and a hollow portion of the base end cylindrical portion 53 are provided on the same straight line, and communicate with each other through an internal space of the shutter housing portion 50.

As illustrated in FIG. 3B, the inner tube 44 can include a stopper 54 fitting to the outer tube 46 so as to be releasable, provided thereon. The stopper 54 is displaceable between an engaging position at which the stopper 54 can engage with the outer tube 46 disposed outside the inner tube 44 (refer to FIG. 3B) and a releasing position that is positioned inside the inner tube 44 beyond the engaging position and at which the engagement with the outer tube 46 is released and the stopper 54 enters the inside of the hollow portion of the base end cylindrical portion 53 (refer to FIG. 9).

In a state where the needlepoint 17 of the inner needle 16 has been positioned on the leading end side beyond the stopper 54, the stopper 54 is pressed outward by the inner needle 16 and engages with the outer tube 46 so that the outer tube 46 is prevented from moving backward with respect to the inner tube 44. Meanwhile, when the needlepoint 17 of the inner needle 16 moves to the base end side beyond the stopper 54, the stopper 54 is displaced in an inward direction and the engagement with the outer tube 46 is released. Thus, the outer tube 46 becomes movable backward with respect to the inner tube 44.

Figure 10:
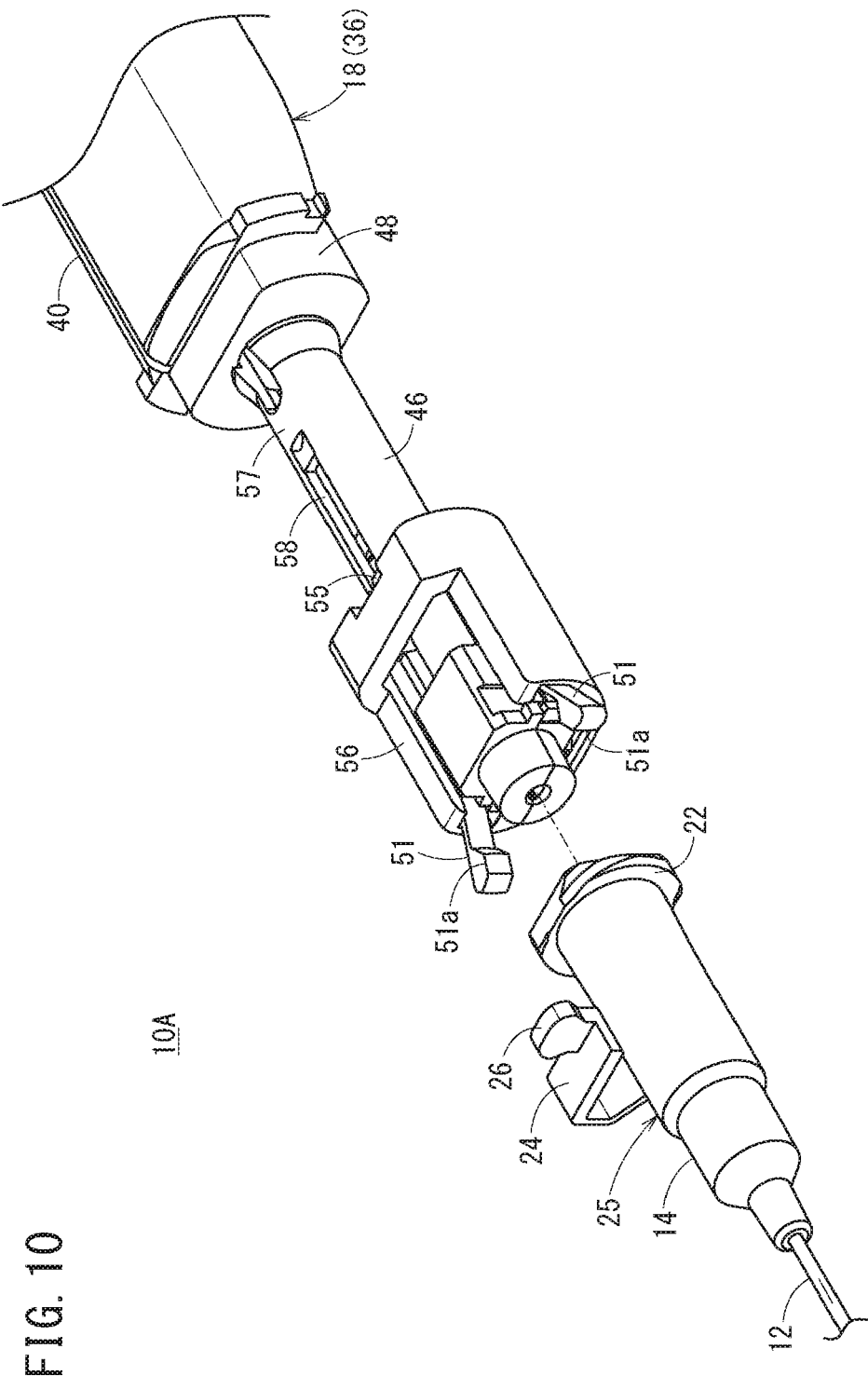
FIG. 10 is a perspective view of the catheter assembly illustrated in FIG. 1 in the state where the catheter hub and the protector have separated from each other.

In FIG. 2, the arms 51 engage with the base end of the catheter hub 14 from the outside so as to be releasable. According to the present embodiment, the arms 51 are provided so as to have a pair on left and right side surfaces of the shutter housing portion 50. Each of the arms 51 is elastically deformable in the left and right direction. A pawl 51a (refer to FIG. 10) capable of engaging with the flange portion 22 of the catheter hub 14, is provided on the inside of a leading end of each of the arms 51. The leading end side of each of the arms 51 inclines so as to expand outward in the leading end direction, in a natural state where no external force acts.

As illustrated in FIGS. 2 and 3B, the outer tube 46 has an arm housing portion 56 capable of housing the arms 51 and a cylindrical portion 57 protruding from the side of a base end of the arm housing portion 56. The arm housing portion 56 can be formed so as to be box shaped having an upper portion and a leading end portion both open. In the initial state of the catheter assembly 10A, the arm housing portion 56 can include the base end of the catheter hub 14 and the side of the leading end of the inner tube 44 (the pair of arms 51 and the shutter housing portion 50) disposed inside.

As illustrated in FIG. 3B, the base end cylindrical portion 53 of the inner tube 44 is inserted into the cylindrical portion 57 of the outer tube 46. Long-hole slits 58 passing through the inside and the outside of the cylindrical portion 57 are provided in an axis line direction of the cylindrical portion 57 so as to have a pair on an upper portion and a lower portion of a part close to a leading end of the cylindrical portion 57. Each protruding portion 55 provided on the inner tube 44 is inserted into each of the slits 58.

In accordance with an exemplary embodiment, first and second outward protrusions 60 and 61 protruding outward and extending in the circumferential direction, can be provided at an interval in the axial direction on an outer surface of a base end of the cylindrical portion 57. An annular groove 62 is formed between the first outward protrusion 60 and the second outward protrusion 61.

The nipple 48 has an intra-cavity capable of housing the cylindrical portion 57 of the outer tube 46. The nipple 48 is assembled to the outer tube 46 so as to be relatively slidable. As illustrated in FIG. 2, an inner hook 64 protruding inward and extending in the circumferential direction, is provided on an inner surface of a leading end of the nipple 48. The inner hook 64 is capable of engaging with the annular groove 62 provided on the outer tube 46 (refer to FIG. 7). A state where the inner hook 64 has engaged with the annular groove 62, helps prevent a relative movement in the axial direction between the outer tube 46 and the nipple 48. Accordingly, the annular groove 62 and the inner hook 64 are included in a first locking mechanism 66 that prevents the relative movement in the axial direction between the outer tube 46 and the nipple 48.

Figure 6:
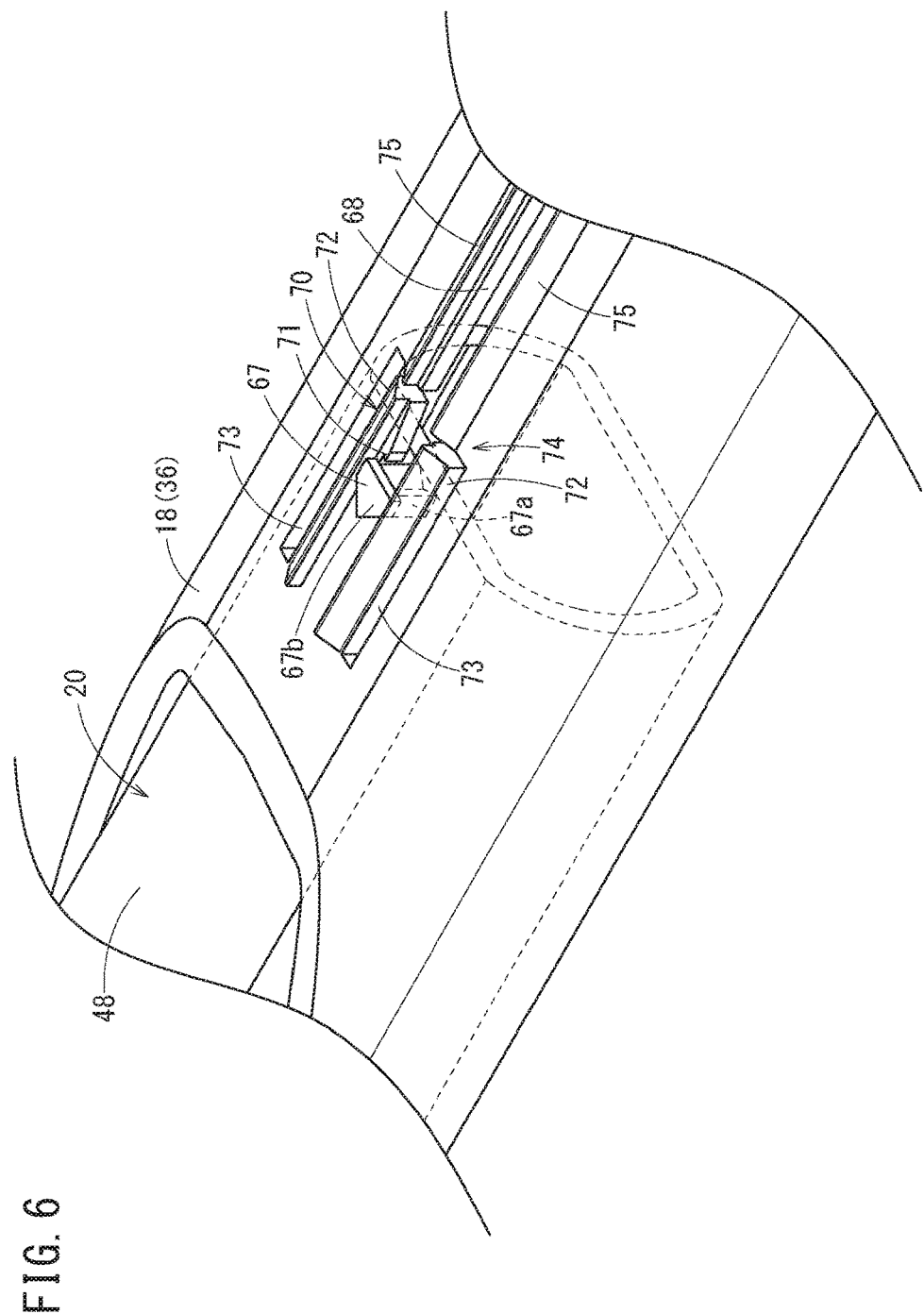
FIG. 6 is a perspective view of the catheter assembly illustrated in FIG. 1 from the bottom side in a state where an engaging portion and an engaging protrusion have engaged with each other.

An outer surface of a base end portion of the nipple 48 can include an engaging protrusion 67 protruding outward (downward in the illustrated example) provided thereon (refer to FIGS. 3A and 6).

FIG. 5A is a bottom view of the catheter assembly 10A in the initial state. As illustrated in FIG. 5A, a lower surface of the housing 18 can include a passage 68 extending in the axial direction and allowing displacement in the axial direction of the engaging protrusion 67 provided on the nipple 48, and an engaging portion 70 disposed on the leading end side of the passage 68, provided thereon. In the initial state, the engaging protrusion 67 is positioned in proximity to a base end of the passage 68. According to the present embodiment, the passage 68 is a hole passing through the inside and the outside of the housing main body 36, but may be a groove provided on an inner surface of the housing main body 36.

FIG. 5B is an enlarged view of the engaging portion 70 and the periphery thereof. The engaging portion 70 has a pair of pawls 71 protruding into the passage 68. The pair of pawls 71 include a pair of engaging arms 72 extending in a base end direction of the housing 18. A slit long hole 73 extending in the axial direction of the outer tube 46 is provided on each of the left and right outsides of the pair of engaging arms 72. Accordingly, the pair of engaging arms 72 is elastically deformable in directions in which the pair of engaging arms 72 comes close to and separates from each other. The engaging portion 70 including the above configuration and the engaging protrusion 67 provided on the nipple 48 are capable of engaging with each other.

As illustrated in FIG. 6, when the protector 20 (the nipple 48 thereof) moves to a predetermined position with respect to the housing 18, the engaging portion 70 and the engaging protrusion 67 engage with each other. Specifically, the pawls 71 provided on the pair of engaging arms 72 hook on both sides of a base end of a columnar portion 67a of the engaging protrusion 67. In a state where the engaging portion 70 and the engaging protrusion 67 have engaged with each other, the movement in the axial direction of the nipple 48 with respect to the housing 18 is prevented. Therefore, the nipple 48 is prevented from coming off the housing 18. In addition, the nipple 48 is prevented from moving backward in the housing 18. In this manner, a second locking mechanism 74 for preventing displacement of the protector 20 with respect to the housing 18 in a state where the protector 20 has covered the needlepoint 17 can include the engaging portion 70 and the engaging protrusion 67.

As illustrated in FIG. 6, the engaging protrusion 67 preferably can include a coming-off prevention protrusion 67b for preventing the engaging protrusion 67 from coming off into the housing 18. The coming-off prevention protrusion 67b protrudes from the columnar portion 67a in a width direction, and is capable of engaging with the outer surface of the housing 18.

As illustrated in FIG. 6, portions on both sides of the passage 68 are preferably present outward beyond the engaging protrusion 67 in the housing 18. Specifically, in FIG. 6, the portions on both sides of the passage 68 are protrusions 75 protruding to the outside of the housing 18 and extending in the axial direction of the housing 18. The above protrusions 75 are provided so that the engaging protrusion 67 can be prevented from touching the skin of the patient.

Examples of a constituent material of the above housing 18 and each of the above members in the protector 20 (the inner needle holding member 38, the inner tube 44, the outer tube 46, the nipple 48) that can be applied include, but are not particularly limited, the materials given in the descriptions of the catheter hub 14. In this case, all of the members may be formed of the same material. Each of the members may be formed of a different material.

The catheter assembly 10A according to the first embodiment is basically constituted as described above. Functions and effects of the catheter assembly 10A will be described below.

As illustrated in FIG. 3A, the catheter assembly 10A in the initial state is in a state to be described below. The inner needle 16 has been inserted into the catheter 12 and the needlepoint 17 has protruded from the leading end of the catheter 12 by the predetermined length. The leading end cylindrical portion 52 of the inner tube 44 has been inserted into the base end of the catheter hub 14. The outer tube 46 has maximally moved to the leading end side in a range movable with respect to the inner tube 44. The catheter 12 and the inner needle 16 have been exposed from the leading end of the housing 18, and the catheter hub 14 and the protector 20 have been housed in the housing 18. The pair of arms 51 provided on the inner tube 44 (refer to FIG. 2) is positioned in the arm housing portion 56 of the outer tube 46 so as to be in a closed state. The pair of arms 51 that has been closed has engaged with the flange portion 22 of the catheter hub 14 so that the catheter hub 14 and the protector 20 including the inner tube 44 have been prevented from separating from each other. The needlepoint 17 of the inner needle 16 has been positioned on the leading end side beyond the stopper 54. The stopper 54 has protruded outward beyond the base end cylindrical portion 53 of the inner tube 44 and has engaged with the outer tube 46. Thus, the outer tube 46 has been prevented from moving in the base end direction with respect to the inner tube 44. Furthermore, the nipple 48 has been maximally inserted into the housing 18. The cylindrical portion 57 of the outer tube 46 has been maximally inserted into the nipple 48.

In the use of the catheter assembly 10A, a user (for example, a medical doctor or a nurse) grips the housing 18 and punctures a blood vessel of a patient with the catheter 12 and the inner needle 16. After the puncture, a finger hooks the tab 26 of the hub operating portion 24 protruding from the housing 18, and presses the hub operating portion 24 in the leading end direction. Accordingly, the catheter hub 14 and the catheter 12 that have been coupled to the hub operating portion 24, move in the leading end direction with respect to the housing 18. Thus, an insertion length of the catheter 12 into the blood vessel increases. Meanwhile, the protector 20 coupled to the catheter hub 14 also moves forward in the housing 18 in accordance with the forward movement of the hub operating portion 24.

When the catheter 12 has been inserted into the blood vessel by a predetermined length, next, the housing 18 is pulled in the base end direction with respect to the catheter member 25. Accordingly, the inner needle 16 moves in the base end direction in the catheter 12, the catheter hub 14, and the protector 20. In this case, the protector 20 is in a state where the protector 20 has not been displaced with respect to the catheter member 25 (a movement stopping state) until the inner needle 16 moves backward by a predetermined amount. Accordingly, the protector 20 extends in accordance with a backward movement of the housing 18. During a process during which the protector 20 extends, the inner needle 16 is evulsed from the catheter 12.

Figure 7:
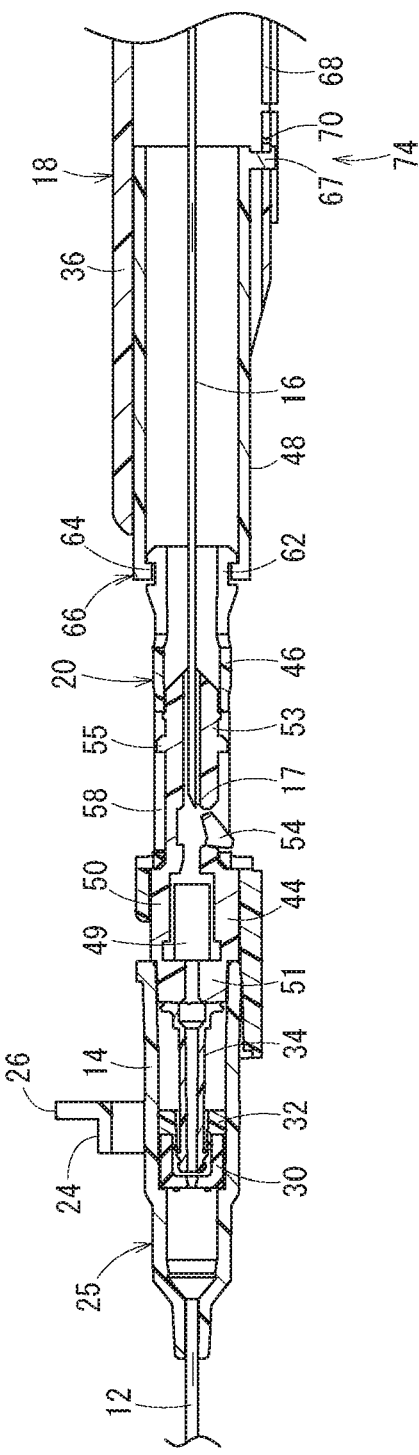
Figure 8:
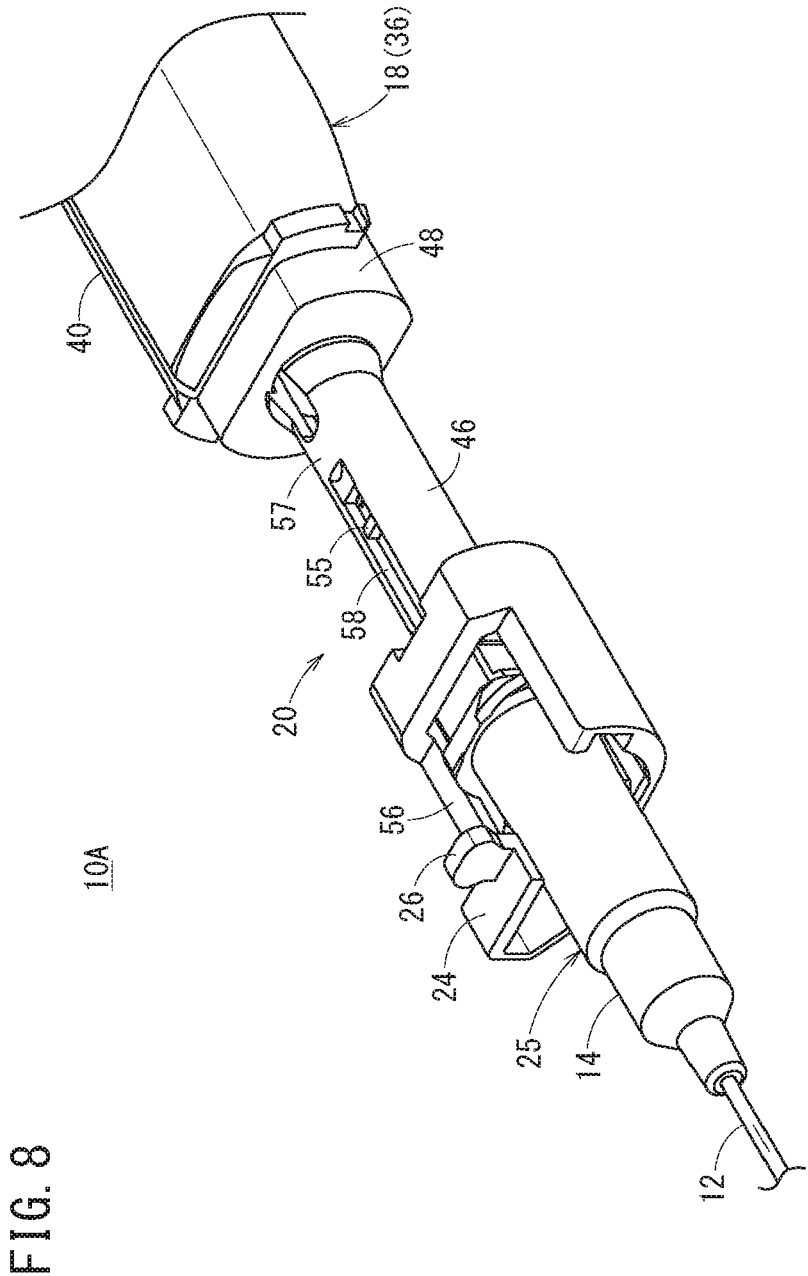

During the process during which the protector 20 extends, the outer tube 46 relatively moves to the side of the leading end of the nipple 48, and the nipple 48 also relatively moves to the side of the leading end of the housing 18. In accordance with the extension of the protector 20, as illustrated in FIG. 7, the engaging portion 70 provided to the housing 18 and the engaging protrusion 67 provided at the base end of the nipple 48 engage with each other. In addition, the annular groove 62 provided at a base end of the outer tube 46 and the inner hook 64 provided at the leading end of the nipple 48 engage with each other. FIG. 8 is a perspective view of the periphery of the protector 20 in this case. In states of FIGS. 7 and 8, a function of the first locking mechanism 66 prevents the movements in the axial direction of the outer tube 46 and the nipple 48. In addition, a function of the second locking mechanism 74 prevents the movements in the axial direction of the nipple 48 and the housing 18.

Meanwhile, during a process during which the housing 18 moves backward with respect to the catheter member 25, the inner needle 16 also moves backward with respect to the inner tube 44. Then, when the needlepoint 17 of the inner needle 16 (refer to FIG. 2) moves to the base end side beyond the shutter member 49 disposed in the inner tube 44, the shutter member 49, in which expansion has been regulated by the pressure from the inner needle 16, expands in the shutter housing portion 50 due to elastic restoring force. As a result, a movement path of the inner needle 16 in the inner tube 44 can be prevented. Thus, the needlepoint 17 of the inner needle 16 can be prevented from protruding again from the leading end of the inner tube 44. Note that, at this point in time at which the needlepoint 17 has moved to the base end side beyond the shutter member 49, the arms 51 provided to the inner tube 44 have been still closed. The engagement between the inner tube 44 and the catheter hub 14 has been retained.

After the engaging portion 70 and the engaging protrusion 67 have engaged with each other and the first and second outward protrusions 60 and 61 and the inner hook 64 have engaged with each other, the needlepoint 17 of the inner needle 16 moves to the base end side beyond the stopper 54 provided to the inner tube 44 (refer to FIG. 7). Accordingly, due to elastic restoring force, the stopper 54 is displaced in an inward direction of the inner tube 44 or at least becomes displaceable in the inward direction of the inner tube 44. From this state, when the housing 18 further operates and moves in the base end direction, the outer tube 46 is displaced in the base end direction with respect to the inner tube 44. A state where the protector 20 has maximally extended can be acquired. Accordingly, the arms 51 expand so that the inner tube 44 separates from the catheter hub 14 (refer to FIGS. 9 and 10).

Specifically, due to the displacement of the outer tube 46 in the base end direction with respect to the inner tube 44, when the arms 51 protrude from the arm housing portion 56 in the leading end direction, the expansion regulation of the arm housing portion 56 with respect to the arms 51 is released. As a result, the arms 51 are actively displaced in an outward direction due to elastic restoring force. Accordingly, the engagement between the arms 51 provided to the inner tube 44 and the flange portion 22 provided to the catheter hub 14 is released. Thus, in accordance with a movement of the housing 18 in the base end direction, the inner tube 44 separates from the catheter hub 14. That is, the catheter hub 14 and the protector 20 separate from each other. A state where only the catheter member 25 out of the catheter assembly 10A has been detained on the side of the patient, can be acquired.

Meanwhile, after the inner needle 16 has been evulsed from the catheter 12, the catheter hub 14 is fixed to the patient with a dressing material or a tape. A connector of a transfusion tube, not illustrated, is coupled to the side of the base end of the catheter hub 14, and supply of a transfusion material (a medical fluid) to the patient through the transfusion tube is performed.

As described above, in the catheter assembly 10A according to the present embodiment, in the initial state, the catheter hub 14 has been housed in the housing 18 (refer to FIG. 3A). Accordingly, an exposure length of the inner needle 16 from the housing 18 can be shortened in comparison to a conventional catheter assembly. Therefore, an entire length of the catheter assembly 10A in the initial state, namely, a length from the base end of the housing 18 to a leading end of the inner needle 16 can be made shorter than a conventional catheter assembly. Accordingly, excellent storage due to compactness is acquired and the puncture operation is easily performed. Since the exposure length of the inner needle 16 from the housing 18 is short, the protector 20 may be also made to be short. Accordingly, an entire product length even in a state where the protector 20 has covered the needlepoint 17 (a needlepoint protecting state), is short. Therefore, a waste is compact, and disposal is relatively easy to perform.

According to the present embodiment, the passage 68 extending in the axial direction is provided on a wall portion included in the housing 18. In addition, the engaging portion 70 protruding in the passage 68 and the engaging protrusion 67 provided to the protector 20 (the nipple 48 thereof) engage with each other so that the displacement of the protector 20 with respect to the housing 18 is prevented (refer to FIG. 6). With this configuration, there is no need for a structure protruding inward in the housing 18 in order to engage the housing 18 and the protector 20. A forward movement of the catheter hub 14 is not hindered. Accordingly, a forward movement operation of the catheter 12 can be performed relatively smoothly.

Specifically, the engaging protrusion 67 can include the coming-off prevention protrusion 67b for preventing the engaging protrusion 67 from coming off into the housing 18, provided thereon (refer to FIG. 6). Accordingly, even in a case where the housing 18 has been deflected, the engagement between the engaging portion 70 and the engaging protrusion 67 is preferably prevented from being released.

According to the present embodiment, the portions on both sides of the passage 68 have been present outward beyond the engaging protrusion 67 in the housing 18 (refer to FIG. 6). Accordingly, the movement of the engaging protrusion 67 can be prevented from being hindered due to contact of the engaging protrusion 67 with the patient. In particular, the portions on both sides of the passage 68 are protrusions 75 protruding to the outside of the housing 18 and extending in the axial direction of the housing 18. Thus, a lower wall of the housing 18 except the protrusions 75 can be set so as to have an appropriate thickness. There is no need for thickening the entire lower wall of the housing 18.

According to the present embodiment, at least the part of the hub operating portion 24 is exposed from the housing 18 (refer to FIG. 1). Accordingly, coming in contact with the hub operating portion 24 exposed from the housing 18 can operate the catheter hub 14. Thus, the forward movement operation of the catheter 12 can be performed relatively easily. In particular, according to the present embodiment, the part of the hub operating portion 24 is exposed to the outside of the housing 18 through the slit 40 provided on the housing 18. Thus, with a simple structure, the hub operating portion 24 can be exposed to the outside of the housing 18.

According to the present embodiment, the slit 40 is provided so as to be shifted to the one side in the left and right direction with respect to the center of the housing 18. Thus, when a puncture is operated, the inner needle 16 can be preferably prevented from being exposed to the outside of the housing 18 through the slit 40.

According to the present embodiment, the coupling portion 27 has flexibility so that the hub operating portion 24 falls to the side of the catheter hub 14. Accordingly, upon using a dressing material in order to fix the catheter hub 14 to the skin of the patient, as illustrated in FIG. 4B, when the hub operating portion 24 falls to the side of the catheter hub 14, it is relatively easy to stick the dressing material without making the hub operating portion 24 an obstacle.

In particular, the coupling portion 27 has the thin-walled portion 29. The length L1 in the axial direction of the coupling portion 27 is larger than the thickness T2 of the thin-walled portion 29. With this configuration, since the coupling portion 27 is barely deflected in the axial direction, a forward movement operation of the catheter hub 14 can be stably performed. In addition, upon fixing the catheter hub 14 to the patient, the coupling portion 27 is easily and laterally deformed (easily falls). Thus, fixing work of the catheter hub 14 can be performed relatively smoothly.

The coupling portion 27 has the pedestal 28 that abuts on the outer surface of the housing 18 so as to be slidable. With this configuration, upon performing the forward movement operation of the catheter hub 14, the housing 18 supports the pedestal 28. Thus, the deflection in the axial direction of the coupling portion 27 can be inhibited, and the stable operation can be performed.

Figure 11:
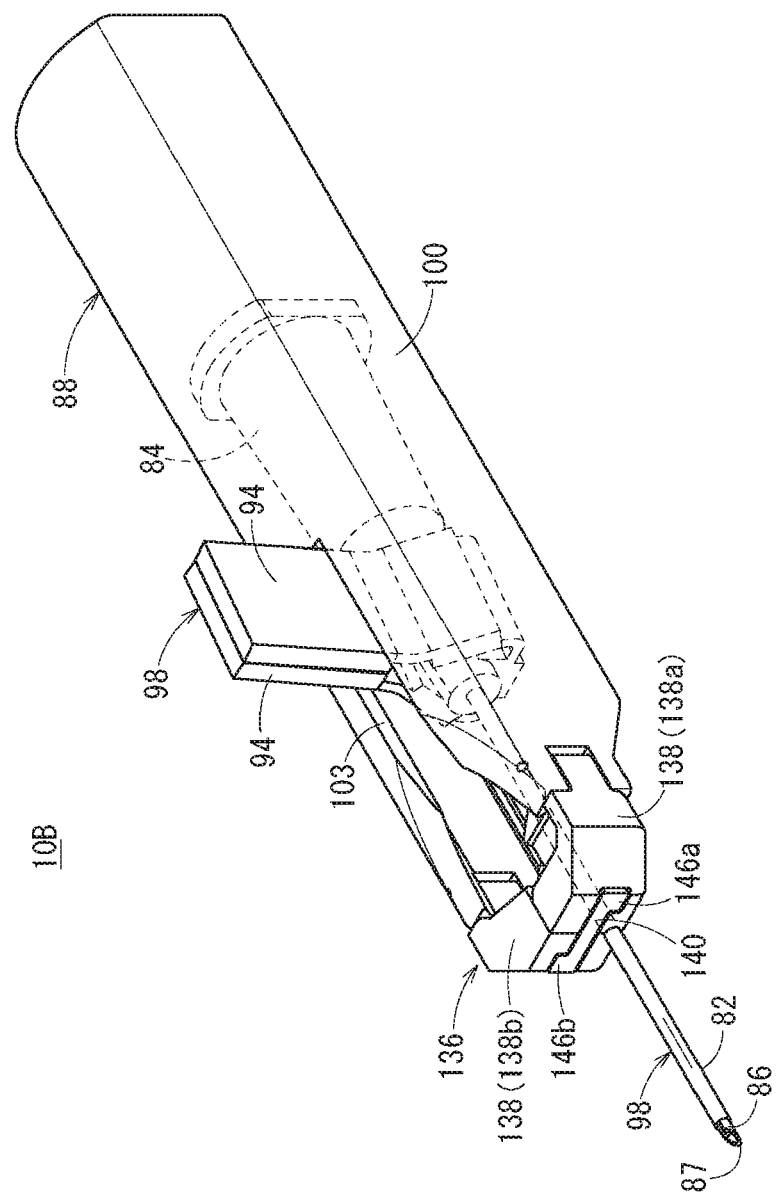
FIG. 11 is a perspective view of a catheter assembly according to a second embodiment of the present disclosure.
Figure 12:
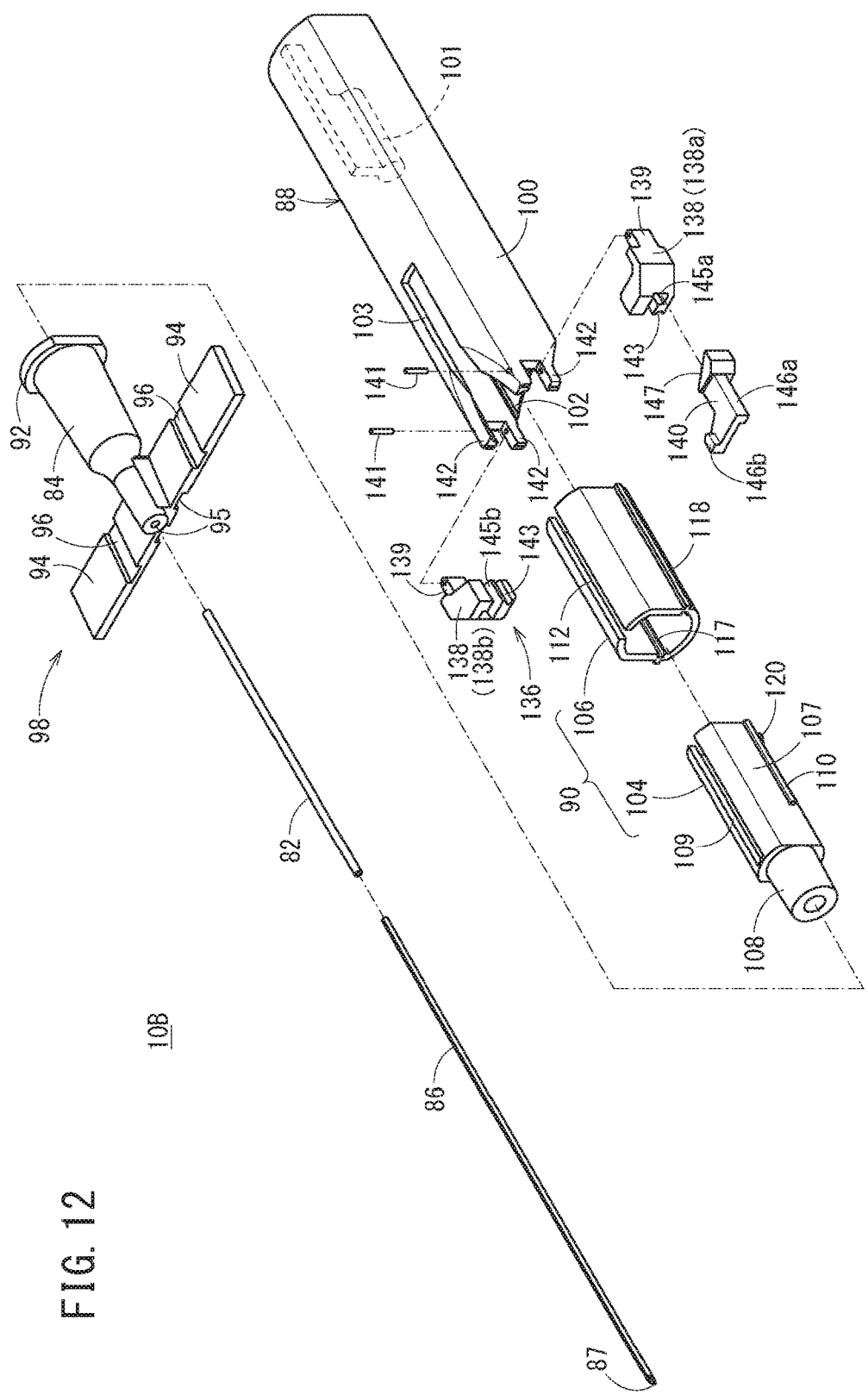
FIG. 12 is an exploded perspective view of the catheter assembly illustrated in FIG. 11.
Figure 13:
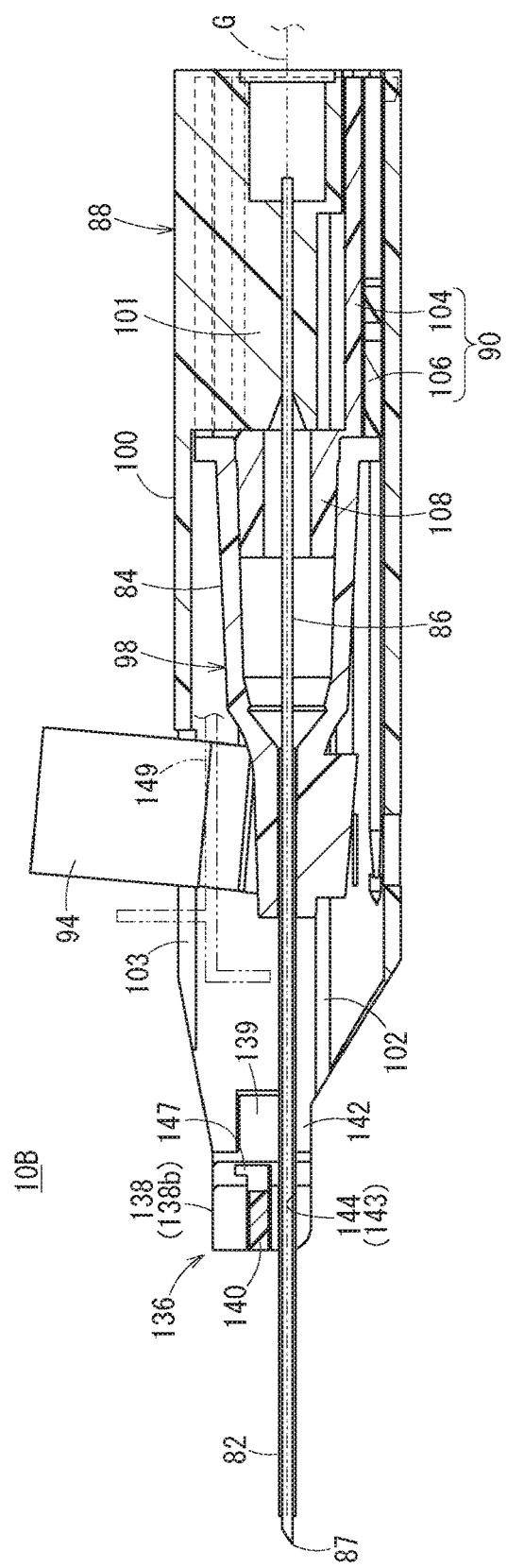
FIG. 13 is a longitudinal-sectional view of the catheter assembly illustrated in FIG. 11.

FIG. 11 is a perspective view of a catheter assembly 10B according to a second embodiment of the present disclosure. FIG. 12 is an exploded perspective view of the catheter assembly 10B. FIG. 13 is a longitudinal-sectional view of the catheter assembly 10B.

The catheter assembly 10B can include a tubular catheter 82 having flexibility, a catheter hub 84 coupled to the side of a base end of the catheter 82, a tubular inner needle 86 having a sharp needlepoint 87 on a leading end and insertable into the inside of the catheter 82, a housing 88 serving as a needle hub coupled to the inner needle 86, and a protector 90 that covers the needlepoint 87 of the inner needle 86 when the inner needle 86 is evulsed.

With the catheter assembly 10B, a user (for example, a medical doctor or a nurse) grips and operates the housing 88 so that a leading end portion of the housing 88 punctures a blood vessel of a patient. The catheter assembly 10B has a double tubular structure in which the inner needle 86 has been inserted into the catheter 82 and the inner needle 86 has protruded from a leading end of the catheter 82 by a predetermined length in an initial state before use (before a puncture to the patient). In the initial state of the catheter assembly 10B, the catheter hub 84 and the housing 88 have been coupled through the protector 90.

The catheter assembly 10B in the initial state can include one assembly having the double tubular structure of the catheter 82 and the inner needle 86, the catheter hub 84, the protector 90, and the housing 88 combined, and is integrally operable.

The hollow cylindrical catheter hub 84 is coupled and fixed to the base end of the catheter 82. A flange portion 92 protruding outward and extending in a circumferential direction is provided on a base end of the catheter hub 84.

The catheter hub 84 can include a pair of wings 94 that protrudes in a left and right direction in a natural state, which is provided thereon. The wings 94 each have flexibility and are foldable so as to overlap with each other. As illustrated in FIG. 12, according to the present embodiment, each of the wings 94 can include a first thin-walled portion 95 provided at a coupling part with the catheter hub 84 and a second thin-walled portion 96 provided on the outside beyond the first thin-walled portion 95. The first thin-walled portion 95 is provided so as to be groove-shaped on the side of a lower surface of each of the wings 94. The second thin-walled portion 96 is provided so as to be groove-shaped on the side of an upper surface of each of the wings 94.

With this configuration, the wings 94 easily fold upward at parts of the first thin-walled portions 95 and easily fold in a direction opposite to the first thin-walled portions 95 at parts of the second thin-walled portions 96. As illustrated in FIG. 11, in the initial state of the catheter assembly 10B, outer end portions of the wings 94 are exposed from the housing 88. The user touches and grips or presses the wings 94 exposed from the housing 88 so that the catheter hub 84 can be operated in an axial direction. That is, the pair of wings 94 functions as a hub operating portion for operating the catheter hub 84.

Hereinafter, a member including the catheter 82, the catheter hub 84, and the pair of wings 94 will be referred to as a "catheter member 98".

As illustrated in FIG. 13, the inner needle 86 is formed sufficiently longer than the catheter 82. In the initial state of the catheter assembly 10B, the needlepoint 87 protrudes from a leading end opening of the catheter 82 by a predetermined length. In addition, in the initial state, the inner needle 86 has a midway part in the longitudinal direction inserted into the inside of the catheter hub 84, and has the side of the base end held inside the housing 88.

As illustrated in FIGS. 12 and 13, the housing 88 can include a hollow housing main body 100 included in a shell to be gripped by the user and an inner needle holding portion 101 provided on the base end side of the housing main body 100. The inner needle holding portion 101 protrudes downward from the center in the left and right direction on the side of the base end of the housing main body 100. A rail groove 102 extending in the axial direction is provided on each of left and right inner surfaces of the housing main body 100.

In the initial state of the catheter assembly 10B, the catheter 82 and the inner needle 86 are exposed from a leading end of the housing 88, and the catheter hub 84 and the protector 90 are housed in the housing 88. As a result, the leading end of the housing 88 protrudes to a midway of the catheter 82. According to the present embodiment, a position of the base end of the catheter hub 84 is positioned on the base end side beyond a position of the center in an axial direction of the housing 88, and the leading end of the housing 88 is positioned on the leading end side beyond a position of the center in a longitudinal direction of the catheter 82.

As illustrated in FIGS. 11 to 13, a slit 103 that extends in the axial direction of the housing 88 and is open on the side of the leading end of the housing 88 is formed in the housing 88 (specifically, the housing main body 100). According to the present embodiment, the slit 103 is formed on an upper wall of the housing 88. In the initial state of the catheter assembly 10B, the outer end portions of the wings 94 that have been folded and overlapped each other protrude upward from the housing 88 through the slit 103.

The protector 90 houses the inner needle 86 in accordance with evulsion of the inner needle 86 from the catheter 82 so as to cover the needlepoint 87 of the inner needle 86. As illustrated in FIGS. 12 and 13, the protector 90 has an inner tube 104 fitting to the base end of the catheter hub 84 so as to be separable, and an outer tube 106 in which the inner tube 104 is disposed on the inside thereof, the outer tube 106 being relatively displaceable in the axial direction in a range regulated with respect to the inner tube 104. Upon the evulsion of the inner needle 86 from the catheter 82, the protector 90 extends so as to cover an entire length of the inner needle 86 (refer to FIG. 18).

The inner tube 104 functions to cover the needlepoint 87 of the inner needle 86 in accordance with the evulsion of the inner needle 86 from the catheter 82. The inner tube 104 has a body portion 107 and a leading end fitting portion 108 protruding from the body portion 107 in the leading end direction. An upper wall of the body portion 107 can include a cutout 109 extending in the axial direction, which is formed thereon. In the initial state, the inner tube 104 is positioned in the base end of the housing 88. The inner needle holding portion 101 of the housing 88 is inserted into the cutout 109 of the body portion 107. Each of left and right outer surfaces of the body portion 107 can include a rail protrusion 110 extending in the axial direction (refer to FIG. 12) provided on the body portion 107.

The leading end fitting portion 108 of the inner tube 104 is formed so as to have a taper shape that decreases in outer diameter as going in the leading end direction. In the initial state, the leading end fitting portion 108 of the inner tube 104 fits into the base end of the catheter hub 84. The inner tube 104 and the catheter hub 84 are coupled due to frictional resistance on a fitting surface.

The outer tube 106 is disposed between the inner tube 104 and the housing 88. An upper wall of the outer tube 106 can include a cutout 112 extending in the axial direction, formed thereon. In the initial state, the outer tube 106 is positioned in the base end of the housing 88 with the inner tube 104. The inner needle holding portion 101 of the housing 88 is inserted into the cutout 112.

A rail groove 117 extending in the axial direction is provided on each of left and right inner surfaces of the outer tube 106. The rail protrusions 110 provided on the inner tube 104 are inserted into the rail grooves 117 provided on the outer tube 106 (refer to FIG. 15). Each of left and right outer surfaces of the outer tube 106 can include a rail protrusion 118 extending in the axial direction provided thereon. The rail protrusions 118 provided on the outer tube 106 are inserted into the rail grooves 102 provided on the housing main body 100 (refer to FIG. 15).

Figure 14:
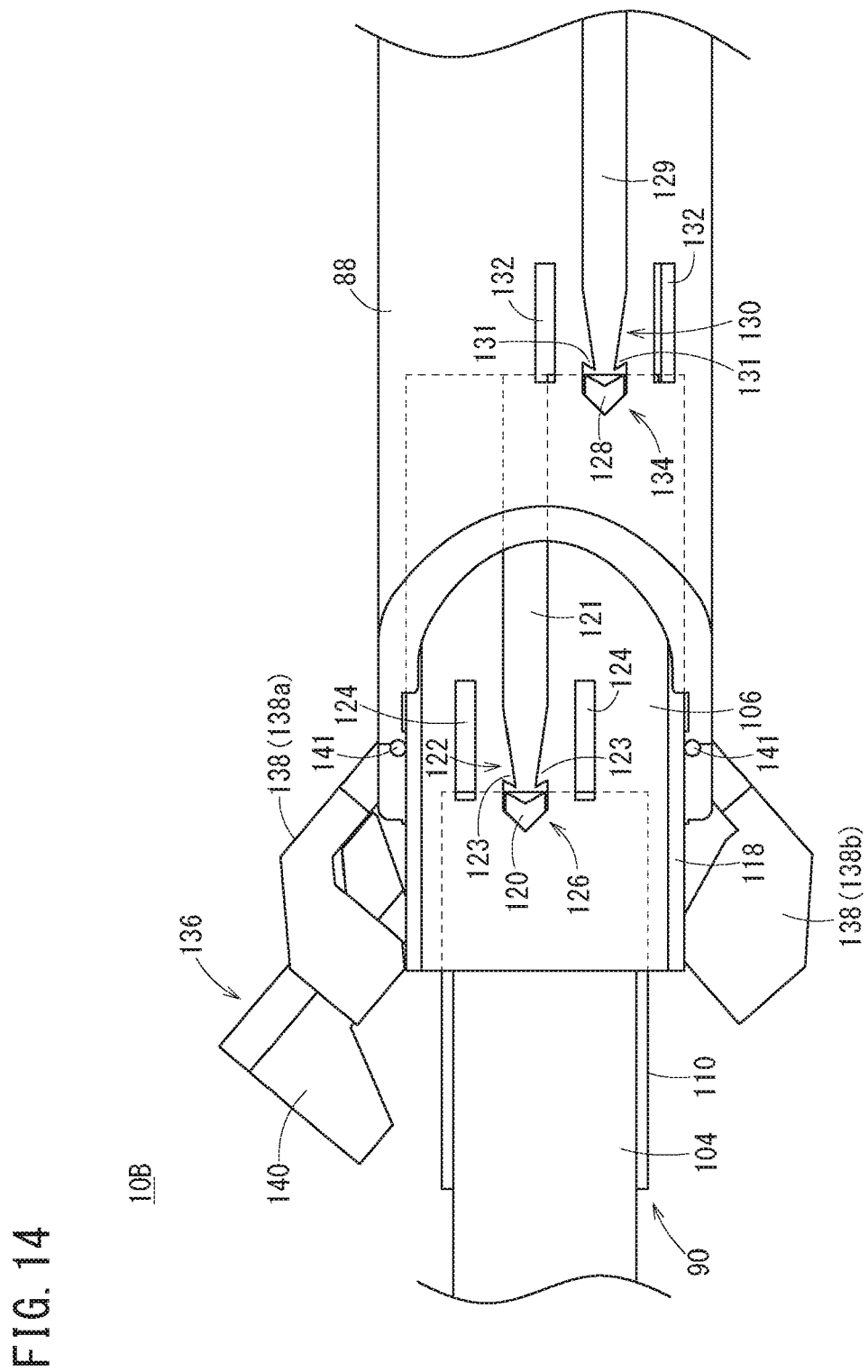
FIG. 14 is a partially omitted rear view of the catheter assembly illustrated in FIG. 11.
Figure 15:
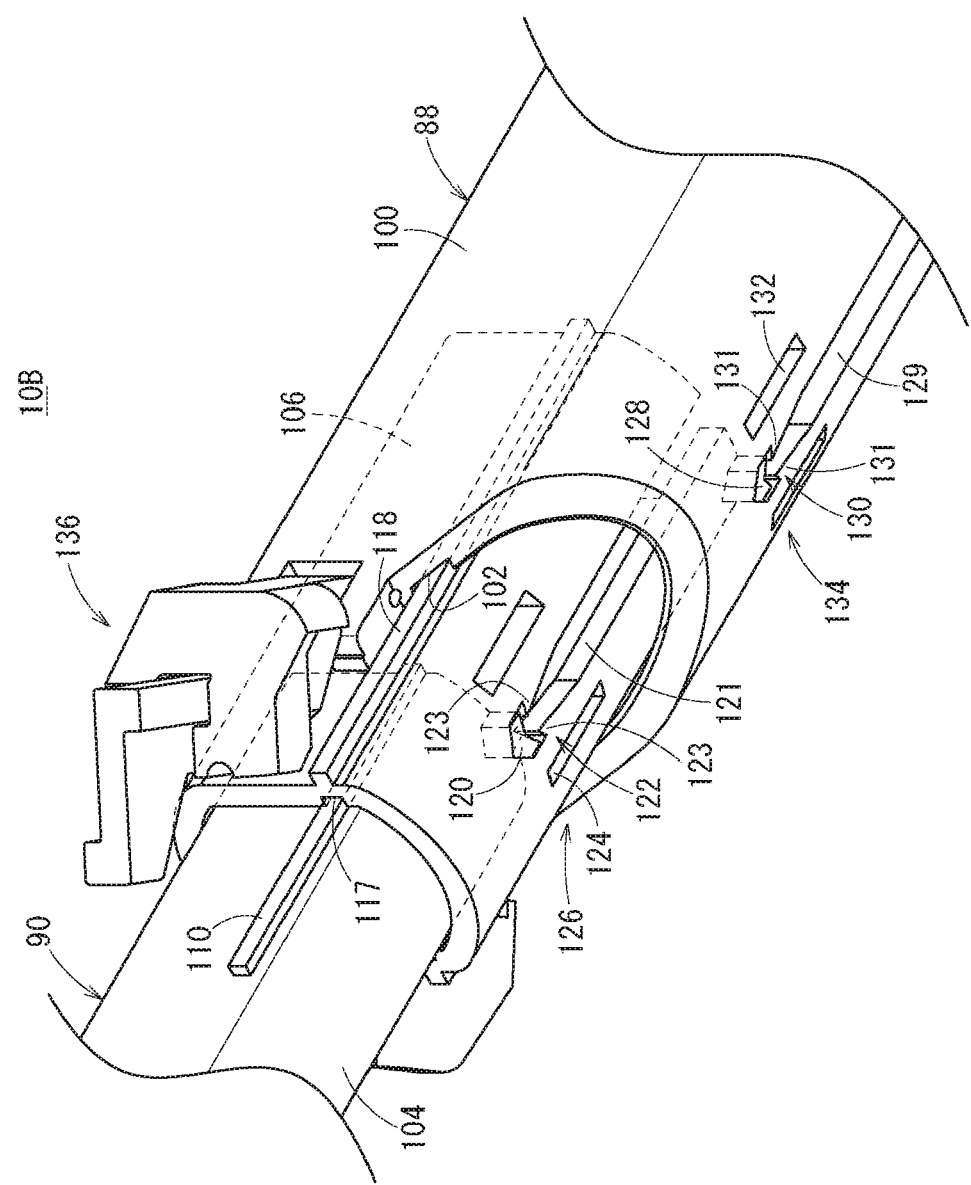
FIG. 15 is a perspective view of the catheter assembly illustrated in FIG. 11 from the bottom side in a state where a first engaging portion and a first engaging protrusion have engaged with each other and a second engaging portion and a second engaging protrusion have engaged with each other.

As illustrated in FIG. 12, an outer surface of a base end portion of the inner tube 104 can include a first engaging protrusion 120 protruding outward (downward in the illustrated example) provided thereon. Meanwhile, as illustrated in FIGS. 14 and 15, the outer tube 106 can include a first passage 121 extending in the axial direction and allowing the first engaging protrusion 120 to be displaced in the axial direction, and a first engaging portion 122 disposed on the side of a lead end of the first passage 121, which are provided thereon. The first passage 121 extends to a base end surface of the outer tube 106. In the initial state of the catheter assembly 10B, the first engaging protrusion 120 is positioned at a base end of the first passage 121. According to the present embodiment, the first passage 121 is a hole passing through the inside and the outside of the outer tube 106, but may be a groove provided on an inner surface of the outer tube 106.

The first engaging portion 122 has a pair of pawls 123 protruding into the first passage 121. A slit long hole 124 extending in the axial direction of the outer tube 106 is provided on each of the left and right outsides of the pair of pawls 123. Accordingly, the pair of pawls 123 is elastically deformable in directions in which the pair of pawls 123 comes close to and separates from each other. The first engaging portion 122 including the above configuration can mutually engage the first engaging protrusion 120 provided on the inner tube 104.

As illustrated in FIGS. 14 and 15, when the inner tube 104 relatively moves forward to a predetermined position with respect to the outer tube 106, the first engaging portion 122 and the first engaging protrusion 120 engage with each other. Specifically, the first engaging protrusion 120 gets over the pair of pawls 123 and the pair of pawls 123 hooks on both sides of a base end of the first engaging protrusion 120. In a state where the first engaging portion 122 and the first engaging protrusion 120 have engaged with each other, a relative movement in the axial direction between the inner tube 104 and the outer tube 106 can be prevented. Therefore, the inner tube 104 can be prevented from coming off the outer tube 106 to the leading end side. In addition, the inner tube 104 can be prevented from moving backward into the outer tube 106.

In this manner, a first locking mechanism 126 for preventing relative displacement in the axial direction between the inner tube 104 and the outer tube 106 in a state where the protector 90 has covered the needlepoint 87 can include the first engaging portion 122 and the first engaging protrusion 120. Note that even in a case where bending stress has acted on the inner tube 104 and the outer tube 106, engaging action between the rail protrusions 110 provided on an outer surface of the inner tube 104 and the rail grooves 117 provided on the inner surface of the outer tube 106 helps prevent the first engaging protrusion 120 from coming off the first engaging portion 122. Accordingly, the function of the first locking mechanism 126 can be preferably retained.

As illustrated in FIGS. 14 and 15, an outer surface of a base end portion of the outer tube 106 can include a second engaging protrusion 128 protruding outward (downward in the illustrated example) provided on the outer surface of the base end portion of the outer tube 106. Meanwhile, the housing 88 (specifically, the housing main body 100) can include a second passage 129 extending in the axial direction and allowing displacement in the axial direction of the second engaging protrusion 128 provided on the outer tube 106, and a second engaging portion 130 disposed on the side of a leading end of the second passage 129, which are provided thereon. The second passage 129 extends to a base end surface of the housing 88. In the initial state of the catheter assembly 10B, the second engaging protrusion 128 is positioned at a base end of the second passage 129. According to the present embodiment, the second passage 129 is a hole passing through the inside and the outside of the housing 88, but may be a groove provided on an inner surface of the housing 88.

The second engaging portion 130 has a pair of pawls 131 protruding into the second passage 129. A slit long hole 132 extending in the axial direction of the housing 88 is provided on each of the left and right outsides of the pair of pawls 131. Accordingly, the pair of pawls 131 is elastically deformable in directions in which the pair of pawls 131 comes close to and separates from each other. The second engaging portion 130 including the above configuration can mutually engage the second engaging protrusion 128 provided on the inner tube 104.

As illustrated in FIGS. 14 and 15, when the outer tube 106 relatively moves forward to a predetermined position with respect to the housing 88, the second engaging portion 130 and the second engaging protrusion 128 engage with each other. Specifically, the second engaging protrusion 128 gets over the pair of pawls 131 and the pair of pawls 131 hooks on both sides of a base end of the second engaging protrusion 128. In a state where the second engaging portion 130 and the second engaging protrusion 128 have engaged with each other, relative displacement in the axial direction between the outer tube 106 and the housing 88 can be prevented. Therefore, the outer tube 106 can be prevented from coming off the housing 88. In addition, the outer tube 106 can be prevented from moving backward into the housing 88.

In this manner, a second locking mechanism 134 for preventing the relative movement in the axial direction between the outer tube 106 and the housing 88 in a state where the protector 90 has covered the needlepoint 87 can include the second engaging portion 130 and the second engaging protrusion 128. Note that even in a case where bending stress has acted on the outer tube 106 and the housing 88, engaging action between the rail protrusions 118 provided on an outer surface of the outer tube 106 and the rail grooves 102 provided on the inner surface of the housing 88 prevents the second engaging protrusion 128 from coming off the second engaging portion 130. Accordingly, the function of the second locking mechanism 134 can be preferably retained.

As illustrated in FIG. 14, the first locking mechanism 126 and the second locking mechanism 134 are disposed so as to be shifted to each other in a circumferential direction.

As illustrated in FIGS. 11 to 13, the catheter assembly 10B further can include a needle support portion 136 in order to inhibit deflection of the inner needle 86 upon a puncture. The needle support portion 136 supports the inner needle 86 through the catheter 82 on the leading end side beyond the catheter hub 84 in the initial state of the catheter assembly 10B. The needle support portion 136 can be movable with respect to the housing 88 in order to change from a first state of supporting the inner needle 86 to a second state of releasing the support with respect to the inner needle 86 and allowing the catheter hub 84 to pass.

According to the present embodiment, specifically, the needle support portion 136 has a pair of support arms 138 openable and closeable and a restraining portion 140 capable of restraining the pair of support arms 138 in a closed state and also releasing the restraint. Hereinafter, in a case where one and the other of the pair of support arms 138 are distinguished from each other and described, the one will be indicated as a "support arm 138a" and the other will be indicated as a "support arm 138b".

The pair of support arms 138 is rotatably coupled to the housing 88 through a pair of support pins 141. In the present illustrated example, each of the pair of support pins 141 has an axis in an upper and lower direction. The pair of support arms 138 supported by the pair of support pins 141 is openable and closeable in a left and right direction.

A coupling protruding portion 139 protruding in the base end direction is provided at a base end of each of the arms 138. Two support protruding portions 142 protruding in the leading end direction are provided on each of the left and right sides of the leading end of the housing 88. The coupling protruding portion 139 provided on each of the support arms 138 is disposed between the two support protruding portions 142 apart from each other in the upper and lower direction and extending in parallel on each of the left and right sides. The support pin 141 is inserted into the two support protruding portions 142 and the coupling protruding portion 139.

Note that, according to a modification, one support protruding portion 142 protruding in the leading end direction may be provided on each of the left and right sides of the leading end of the housing 88. Alternatively, according to another modification, two coupling protruding portions 139 apart from each other in the upper and lower direction and extending in parallel may be provided at the base end of each of the support arms 138. One support protruding portion 142 protruding in the leading end direction may be provided on each of the left and right sides of the leading end of the housing 88.

In each of the support arms 138, a support groove 143 for holding the inner needle 86 in a state where the pair of support arms 138 has been closed is provided. In the state where the pair of support arms 138 has been closed, the two support grooves 143 form a support hole 144 for supporting the inner needle 86. The support hole 144 extends in the axial direction of the housing 88, namely, in a direction in which the inner needle 86 extends in the initial state.

One of the support arms 138 has a bending engaging groove 145a provided thereon and the other has a bending engaging groove 145b provided thereon when viewed from the front side in the closed state. The engaging grooves 145a and 145b pass through the support arms 138a and 138b, respectively, in a longitudinal direction. One engaging groove 145a (hereinafter, referred to as a "first engaging groove 145a") and the other engaging groove 145b (hereinafter, referred to as a "second engaging groove 145b") mutually bend in opposite directions. Specifically, the first engaging groove 145a bends downward and the second engaging groove 145b bends upward.

The restraining portion 140 is disposed slidable with respect to the pair of support arms 138. The restraining portion 140 is pressed by the catheter hub 84 in accordance with a forward movement of the catheter hub 84 so that the restraint with respect to the pair of the support arms 138 is released.

Specifically, the restraining portion 140 has a first restraining protrusion 146a engaging with the first engaging groove 145a so as to be slidable and a second restraining protrusion 146b engaging with the second engaging groove 145b so as to be slidable. In the present illustrated example, the first restraining protrusion 146a and the second restraining protrusion 146b mutually protrude in opposite directions so as to fit to shapes of the first engaging groove 145a and the second engaging groove 145b provided on the pair of support arms 138, respectively. When the restraining portion 140 is positioned at an initial position (a backward position), the first restraining protrusion 146a and the second restraining protrusion 146b of the restraining portion 140 engage with the first engaging groove 145a and the second engaging groove 145b of the pair of support arms 138, respectively. Accordingly, the pair of support arms 138 is restrained in the closed state.

The second restraining protrusion 146b separates from the second engaging groove 145b of the support arm 138b in the leading end direction in accordance with a movement of the restraining portion 140 in the leading end direction. When the second restraining protrusion 146b separates from the second engaging groove 145b, the restraint of the restraining portion 140 with respect to the pair of support arms 138 is released and the pair of support arms 138 becomes expansible. Note that, even after the second restraining protrusion 146b has separated from the second engaging groove 145b, engagement between the first restraining protrusion 146a and the first engaging groove 145a is retained so that the restraining portion 140 is held by the support arm 138a.

In a state where the second restraining protrusion 146b has separated from the second engaging groove 145b, the second restraining protrusion 146b protrudes to the side opposite to the side on which the inner needle 86 is present (refer to FIG. 16B). Accordingly, when the support arm 138a opens in a state where the inner needle 86 has bended to the side of the restraining portion 140, the inner needle 86 is prevented from being hooked on the second restraining protrusion 146b. Note that, according to a modification, the second restraining protrusion 146b may protrude to the side on which the inner needle 86 is present. In this case, a bending shape of the second engaging groove 145b to be provided to the support arm 138b, is formed so as to be in a direction in which the second restraining protrusion 146b protrudes.

A base end of the restraining portion 140 can include a portion to be pressed 147 provided thereat. Upon a forward movement of the catheter hub 84 with respect to the housing 88, the leading end of the catheter hub 84 pressed the portion to be pressed 147 so that the restraining portion 140 moves forward with respect to the pair of support arms 138. A surface of the portion to be pressed 147 facing the catheter hub 84 can include a taper that inclines so as to be displaced outward in the left and right direction as going in the base end direction, provided thereon.

Note that the respective members in the catheter assembly 10B according to the second embodiment, having the same terms as those in the catheter assembly 10A according to the first embodiment include the materials exemplified as constituent materials of those of the catheter assembly 10A.

The catheter assembly 10B according to the second embodiment is basically constituted as described above. Functions and effects of the catheter assembly 10B will be described below.

As illustrated in FIGS. 11 and 13, the catheter assembly 10B in the initial state is in a state to be described below. The inner needle 86 has been inserted into the catheter 82 and the needlepoint 87 has protruded from the leading end of the catheter 82 by the predetermined length. The leading end fitting portion 108 of the inner tube 104 has been inserted into the base end of the catheter hub 84. The outer tube 106 has maximally moved to the leading end side in a movable range with respect to the inner tube 104. The catheter 82 and the inner needle 86 have been exposed from the leading end of the housing 88, and the catheter hub 84 and the protector 90 have been housed in the housing 88. The protector 90 is positioned on the base end side in the housing 88. The restraining portion 140 has been positioned at the backward position in a movable range. The pair of support arms 138 has been restrained in the closed state by the restraining portion 140. The inner needle 86 has been held by the pair of support arms 138 in the closed state through the catheter 82.

In the use of the catheter assembly 10B, a user (for example, a medical doctor or a nurse) grips the housing 88 and punctures a blood vessel of a patient with the catheter 82 and the inner needle 86. In this case, the inner needle 86 has been supported by a support hole 144 formed between the pair of support arms 138 that has been closed, through the catheter 82, so that the deflection of the inner needle 86 is inhibited upon the puncture. Accordingly, a stable puncture can be performed.

After the puncture, a finger hooks the pair of wings 94 protruding from the housing 88, and pressed the pair of wings 94 in the leading end direction. Accordingly, the catheter hub 84 and the catheter 82 that have been coupled to the pair of wings 94, move in the leading end direction with respect to the housing 88. Thus, an insertion length of the catheter 82 into the blood vessel increases. Meanwhile, the protector 90 coupled to the catheter hub 84 also moves forward in the housing 88 in accordance with the forward movement operation of the wings 94.

As illustrated in FIGS. 16A and 16B, the catheter hub 84 presses the restraining portion 140 in the leading end direction in accordance with the forward movement of the catheter hub 84. Accordingly, the restraining portion 140 moves in the leading end direction with respect to the pair of support arms 138, and the second restraining protrusion 146b separates from the second engaging groove 145b. The second restraining protrusion 146b separates from the second engaging groove 145b so that the restraint of the restraining portion 140 with respect to the pair of support arms 138 is released and the pair of support arms 138 becomes expansible. After that, the pair of support arms 138 is pressed from the rear side by the catheter hub 84 and expands in accordance with a further forward movement of the catheter hub 84.

After the catheter 82 has been inserted into the blood vessel by a predetermined length, the housing 88 is next pulled in the base end direction in a state where a position of the catheter member 98 has been held. Accordingly, the inner needle 86 moves in the base end direction in the catheter 82, the catheter hub 84, and the protector 90. In this case, since the leading end fitting portion 108 of the inner tube 104 of the protector 90 and the catheter hub 84 have fitted to each other due to predetermined fitting force, the protector 90 extends in accordance with the backward movement of the housing 88. Specifically, the inner tube 104 relatively moves to the side of a leading end of the outer tube 106 and the outer tube 106 also relatively moves to the side of the leading end of the housing 88. After a while, a state where the protector 90 has maximally extended is acquired (refer to FIGS. 17A and 17B). During a process during which the protector 90 maximally extends, the inner needle 86 is evulsed from the catheter 82. In addition, the inner needle 86 is housed in the protector 90 with the needlepoint 87.

In a state where the protector 90 has maximally extended, as illustrated in FIGS. 14 and 15, a function of the first locking mechanism 126 prevents the relative movement in the axial direction between the inner tube 104 and the outer tube 106. In addition, a function of the second locking mechanism 134 prevents the relative movement in the axial direction between the outer tube 106 and the housing 88.

Specifically, in the first locking mechanism 126, since the first engaging protrusion 120 has been positioned at the maximum leading end position of the first passage 121, the inner tube 104 cannot move any further in the leading end direction with respect to the outer tube 106. In the first locking mechanism 126, since the first engaging protrusion 120 and the first engaging portion 122 has engaged with each other, the inner tube 104 cannot move in the base end direction with respect to the outer tube 106.

In the second locking mechanism 134, since the second engaging protrusion 128 has been positioned at the maximum leading end position of the second passage 129, the outer tube 106 cannot move any further in the leading end direction with respect to the housing 88. In the second locking mechanism 134, since the second engaging protrusion 128 and the second engaging portion 130 have engaged with each other, the outer tube 106 cannot move in the base end direction with respect to the housing 88.

Figure 17A:
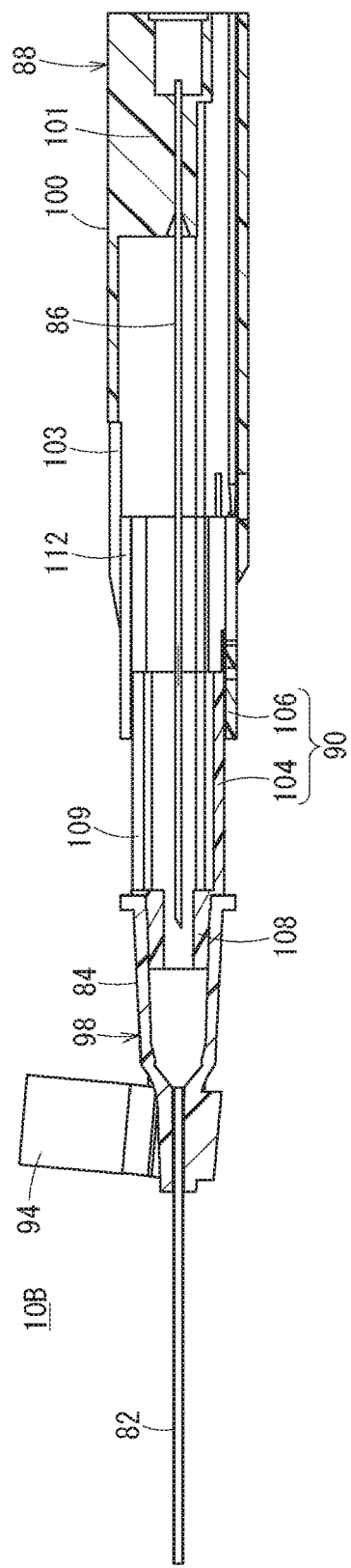
FIG. 17A is a longitudinal-sectional view of the catheter assembly illustrated in FIG. 11 in a state where a protector has maximally extended.
Figure 17B:
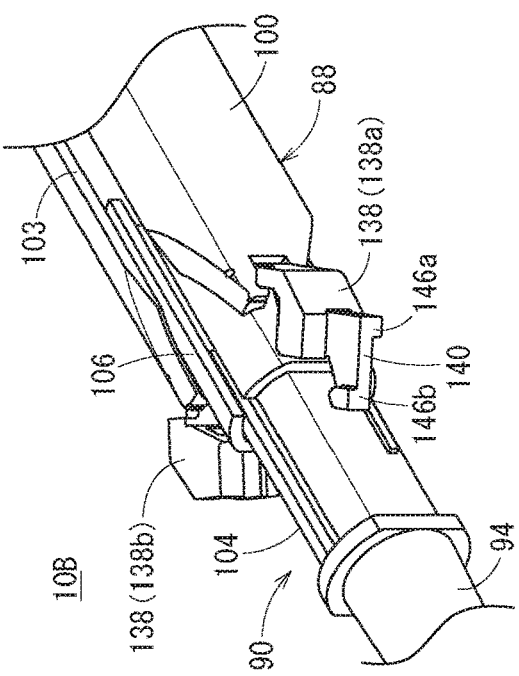
FIG. 17B is a perspective view of the catheter assembly illustrated in FIG. 11 in the state where a protector has maximally extended.

During a process during which the catheter assembly 10B is transferred from a state in FIG. 16A to a state in FIG. 17A, the pair of support arms 138 is pressed from the rear side by the catheter hub 84 so as to expand and allow movements of the catheter hub 84 and the protector 90 with respect to the housing 88 (refer to FIG. 17B). In this manner, the needle support portion 136 supports the inner needle 86 in the initial state and inhibits or prevents the deflection of the inner needle 86 upon the puncture. Meanwhile, after the puncture, the pair of support arms 138 opens so as to prevent interference with the catheter hub 84 and the protector 90.

Figure 18:
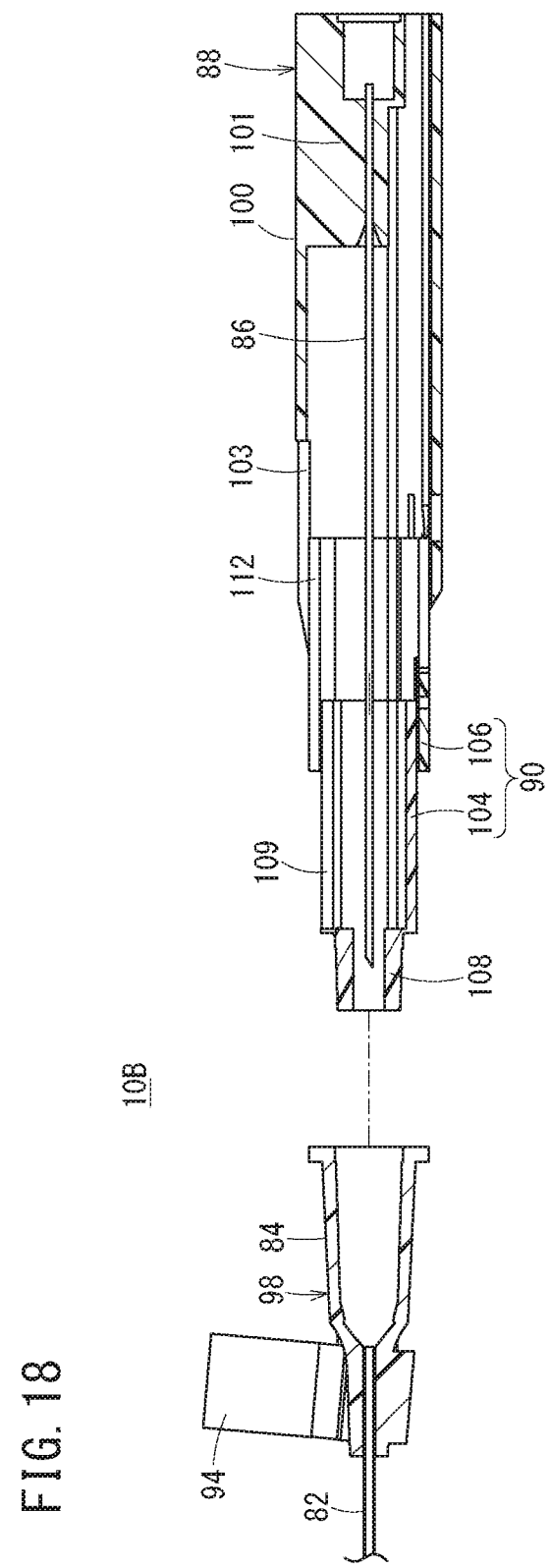
FIG. 18 is a longitudinal-sectional view of the catheter assembly illustrated in FIG. 11 in a state where the catheter hub and the protector have separated from each other.

After the protector 90 has maximally extended, when the housing 88 is further pulled in the base end direction with respect to the catheter member 98, as illustrated in FIG. 18, the fit between the catheter hub 84 and the leading end fitting portion 108 of the inner tube 104 comes off. Accordingly, a state where the protector 90 has completely separated from the catheter member 98 and only the catheter member 98 out of the catheter assembly 10B has been detained on the side of the patient, is acquired.

After the catheter member 98 and the protector 90 have separated from each other, the pair of wings 94 provided on the catheter hub 84 expands in the left and right direction. The pair of wings 94 is fixed to skin of the patient with a tape or the like so as to fix the catheter hub 84. In accordance with an exemplary embodiment, a connector of a transfusion tube, not illustrated, can be coupled to the side of the base end of the catheter hub 84, and supply of a transfusion material (a medical fluid) to the patient through the transfusion tube is performed.

As described above, the catheter assembly 10B according to the second embodiment can include the catheter hub 84 housed in the housing 88 in the initial state. Thus, as in the first embodiment, an entire product length can be shortened in both of the initial state and the needlepoint protecting state due to the protector 90. According to the second embodiment, other respective constituent portions shared with the first embodiment acquire functions and effects similar to those according to the first embodiment.

According to the second embodiment, since the pair of wings 94 functions as the operating portion for the catheter hub 84 in the initial state, there is no need for providing an exclusive operating portion to the catheter hub 84. Thus, the configuration can be simplified.

Furthermore, according to the second embodiment, the needle support portion 136 for supporting the inner needle 86 through the catheter 82 on the leading end side beyond the catheter hub 84, is provided. The needle support portion 136 is provided movable with respect to the housing 88 in order to change from the first state of supporting the inner needle 86 to the second state of releasing the support of the inner needle 86 and allowing the catheter hub 84 to pass.

With this configuration, the deflection of the inner needle 86 upon a puncture is inhibited, and a stable puncture can be performed.

In particular, the needle support portion 136 can include the pair of support arms 138 openable and closeable, and the restraining portion 140 capable of restraining the pair of support arms 138 in the closed state and releasing the restraint. With this configuration, the pair of support arms 138 can securely support the inner needle 86 upon a puncture. In addition, upon the forward movement of the catheter hub 84, the pair of support arms 138 opens so that the movement of the catheter hub 84 with respect to the housing 88 can be securely allowed.

The restraining portion 140 is slidable with respect to the pair of support arms 138. In accordance with a forward movement of the catheter hub 84, the restraining portion 140 is pressed by the catheter hub 84 so that the restraint with respect to the pair of support arms 138 is released. With this configuration, the restraint with respect to the pair of support arms 138 is automatically released in response to the forward movement operation of the catheter hub 84. Thus, there is no need for an independent release operation. Therefore, excellent operability can be acquired.

Note that the hinge structure in which each of the support arms 138 is coupled to the housing 88 so as to rotatable, is not limited to the structure including the above support pin 141. For example, the pair of support arms 138 and the housing 88 may be included in a structure integrally formed through a thin-walled portion. In this case, the thin-walled portion functions as a bending portion so that the pair of support arms 138 is rotatable with respect to the housing 88.

Instead of the configuration in which the pair of support arms 138 is supported so as to be rotatable by the pair of support pins 141 perpendicular to the axial direction of the housing 88, the pair of support arms 138 may be supported so as to be rotatable by a pair of support pins parallel to the axial direction of the housing 88. With this configuration, the pair of support arms 138 is openable and closeable in the left and right direction.

The configuration in which the pair of support arms 138 is openable and closeable in the left and right direction, is not limited to the configuration including the hinge structure. For example, the pair of support arms 138 may be slidable in a width direction of the housing 88 (the left and right direction) so as to be openable and closeable.

In the above configuration, each of the support arms 138 can include the support groove 143 provided thereon, and the two support grooves 143 form the support hole 144. Thus, a position of a contact surface between the support arms 138 in the left and right direction is substantially the same as a position of the center of the inner needle 86 supported by the support hole 144. Accordingly, in a case where predetermined force or more acts on the inner needle 86 in the upper and lower direction, there is a possibility that the inner needle 86 comes off the pair of support arms 138 that has been closed. Therefore, a configuration in which the position of a contact surface between the pair of support arms 138 is shifted in the left and right direction with respect to the center of the inner needle 86 supported by the support hole 144, is provided. Thus, even when force in the upper and lower direction acts on the inner needle 86, the inner needle 86 barely comes off the pair of support arms 138 that has been closed. An example of the above configuration is that at least a support groove having a depth larger than an outer diameter of the catheter 82 is provided on only one of the pair of support arms 138, and the support groove and an inner surface of the other of the pair of support arms 138 form a support hole 144.

In the above configuration, the catheter hub 84 presses the restraining portion 140 so that the restraint with respect to the pair of support arms 138 is released. Instead of this type of configuration, the wings 94 may press the restraining portion 140, and the restraint with respect to the pair of support arms 138 may be released. Alternatively, the catheter assembly 10B may further include a guide wire G inserted into the inner needle 86, and a guide wire operating portion 149 for operating the guide wire G, the guide wire operating portion 149 being coupled to the guide wire G (refer to FIG. 13). In this case, the guide wire operating portion 149 may press the restraining portion 140 in accordance with a forward movement of the guide wire operating portion 149. Thus, the restraint with respect to the pair of support arms 138 may be released.

Figure 19:
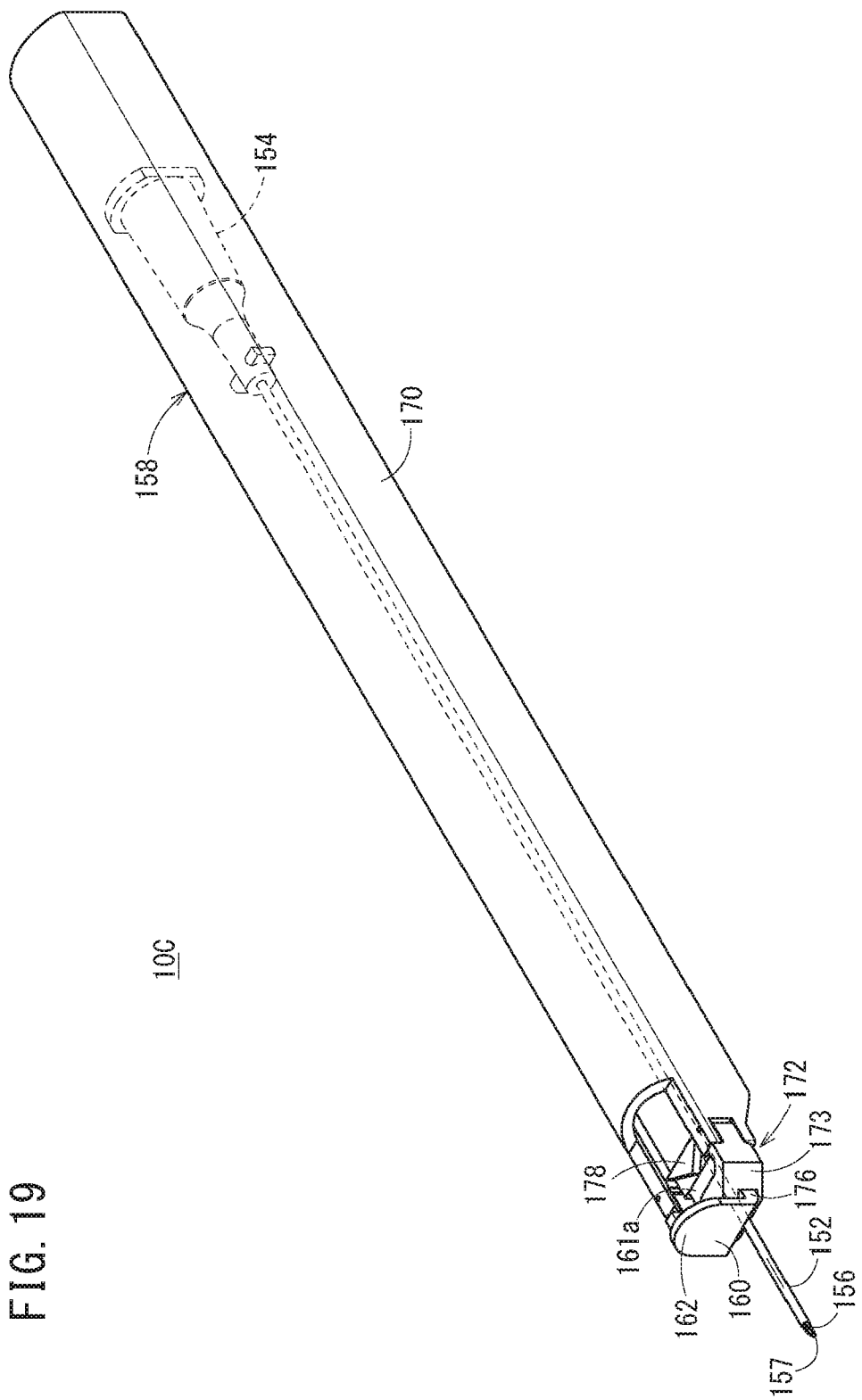
FIG. 19 is a perspective view of a catheter assembly according to a third embodiment of the present disclosure.
Figure 20:
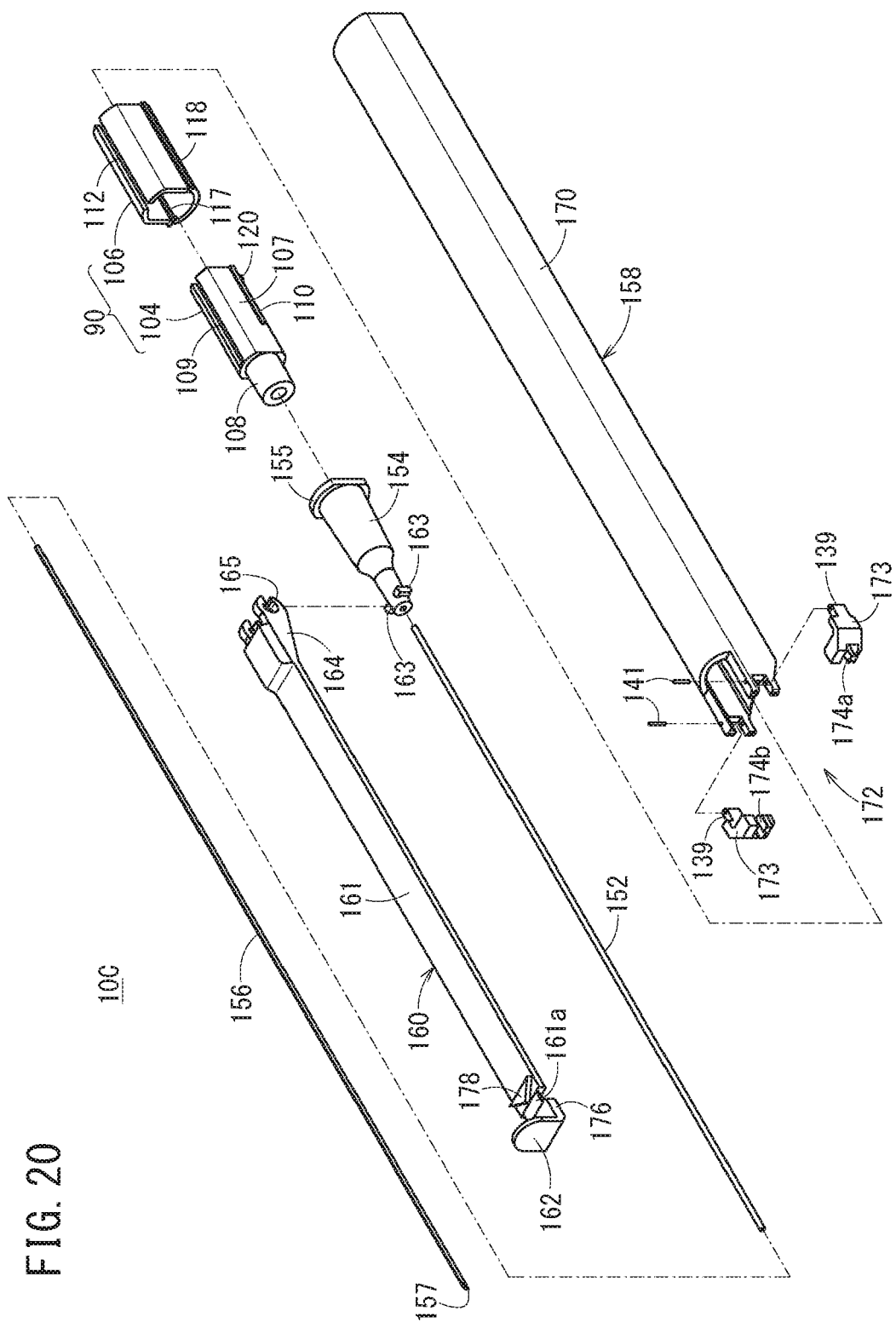
FIG. 20 is an exploded perspective view of the catheter assembly illustrated in FIG. 19.

FIG. 19 is a perspective view of a catheter assembly 10C according to a third embodiment of the present disclosure. FIG. 20 is an exploded perspective view of the catheter assembly 10C. FIG. 21 is a partially omitted longitudinal-sectional view of the catheter assembly 10C. Note that, in the catheter assembly 10C according to the third embodiment, elements having functions and effects the same as or similar to those of the catheter assembly 10B according to the second embodiment, are denoted with the same reference signs, and the duplicate descriptions thereof will be omitted.

The catheter assembly 10C can include a tubular catheter 152 having flexibility, a catheter hub 154 coupled to the side of a base end of the catheter 152, a tubular inner needle 156 having a sharp needlepoint 157 on a leading end and insertable into the inside of the catheter 152, a housing 158 coupled to the inner needle 156, and a protector 90 that covers the needlepoint 157 of the inner needle 156 when the inner needle 156 is evulsed.

A user (for example, a medical doctor or a nurse) grips and operates the housing 158 so that a leading end portion of the catheter assembly 10C punctures a blood vessel of a patient. In accordance with an exemplary embodiment, the catheter assembly 10C has a double tubular structure in which the inner needle 156 has been inserted into the catheter 152 and the inner needle 156 has protruded from a leading end of the catheter 152 by a predetermined length in an initial state before use (before a puncture to the patient). In the initial state of the catheter assembly 10C, the side of a base end of the catheter hub 154 and the side of a leading end of the housing 158 have been coupled through a protector 90.

The catheter assembly 10C in the initial state can include one assembly having the double tubular structure of the catheter 152 and the inner needle 156, the catheter hub 154, the protector 90, and the housing 158 combined, and is integrally operable.

The catheter 152 according to the third embodiment is longer than the catheters 12 and 82 according to the first and second embodiments, respectively. The catheter 152 may be used as a catheter, for example, a central venous catheter, a PICC, or a midline catheter, longer than a peripheral venous catheter in length. Note that the catheter 152 may be used as the peripheral venous catheter.

The hollow cylindrical catheter hub 154 is coupled and fixed to a base end of the catheter 152. A flange portion 155 protruding outward and extending in a circumferential direction, is provided on a base end of the catheter hub 154.

The catheter hub 154 is provided with a hub operating portion 160 for operating the catheter hub 154. In the initial state of the catheter assembly 10C, at least a part of the hub operating portion 160 has been exposed from the housing 158. Specifically, in the initial state, the hub operating portion 160 extends along the inner needle 156 and the catheter hub 154. In addition, a base end portion is coupled to the catheter hub 154, and a leading end portion is exposed on the side of the leading end of the housing 158.

The hub operating portion 160 has a long main body portion 161 and a tab 162 to be hooked by a finger, the tab 162 being provided at a leading end of the main body portion 161. The tab 162 protrudes upward from the leading end of the main body portion 161.

The hub operating portion 160 is coupled to the catheter hub 154 so as to be rotatable. In the present illustrated example, a support protrusion 163 protruding outward is provided on an outer surface on each of the left and right sides of the catheter hub 154. Each of the support protrusions 163 extends in an upper and lower direction. Meanwhile, a base end portion of the main body portion 161 can include a pair of coupling pieces 164 each having a coupling groove 165 and facing each other on the left and right sides, provided thereon.

Figure 22A:
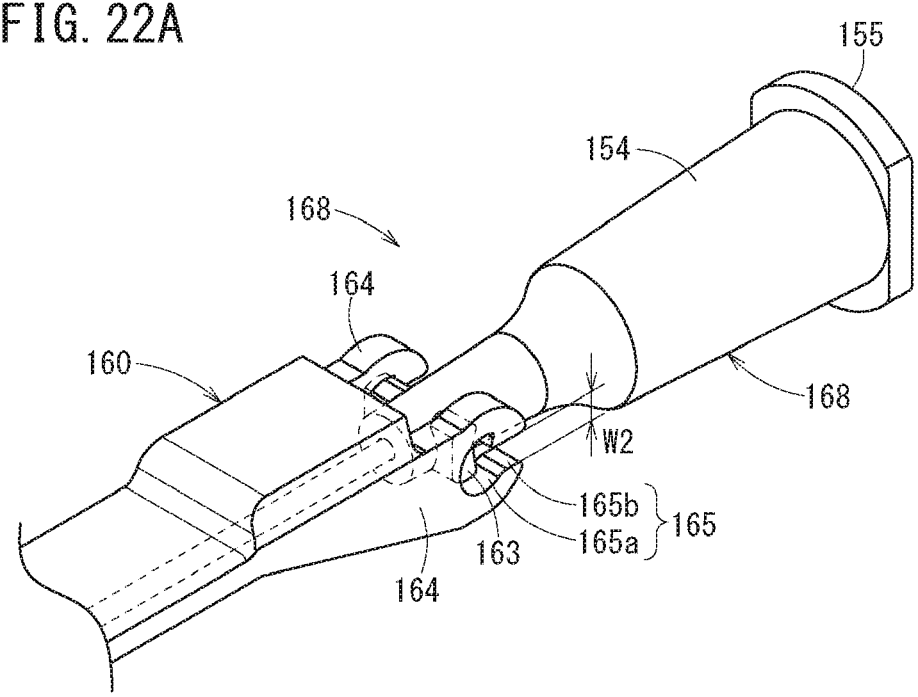
FIG. 22A is a perspective view of a coupling state between a catheter hub and a hub operating portion.

As illustrated in FIG. 22A, each of the coupling grooves 165 can include a first groove 165a for engagement and a second groove 165b for separation having a groove width narrower than the first groove 165a, extending from the first groove 165a in a base end direction, and reaching a base end surface of the coupling piece 164. In accordance with an exemplary embodiment, the groove width W2 of the second grooves 165b can be slightly larger than a width W1 of the support protrusions 163 (refer to FIG. 22B). Each of the support protrusions 163 provided to the catheter hub 154 is inserted into each of the first grooves 165a provided to the hub operating portion 160. Accordingly, the hub operating portion 160 has the support protrusions 163 as axial portions and is supported so as to be rotatable with respect to the catheter hub 154. In the initial state, the hub operating portion 160 is substantially parallel to the catheter 152 and the inner needle 156, and each of the support protrusions 163 engages with each of the first grooves 165a. Thus, the hub operating portion 160 is prevented from separating from the catheter hub 154.

Figure 22B:
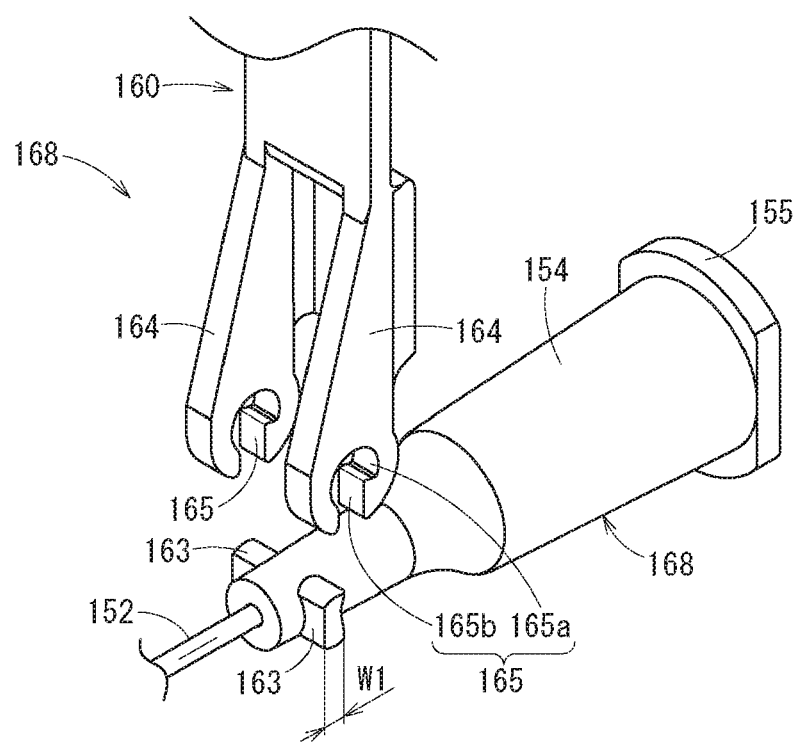
FIG. 22B is a perspective view of a separating state between the catheter hub and the hub operating portion.

As illustrated in FIG. 22B, since extending directions of the support protrusions 163 and the second grooves 165b become the same at a position at which the hub operating portion 160 is substantially perpendicular to an axial direction of the catheter hub 154, the hub operating portion 160 is separable from the catheter hub 154. Note that a constituent material of the hub operating portion 160 is not particularly limited, and may be the same as a constituent material of the catheter hub 154 for example.

Hereinafter, a member including the catheter 152, the catheter hub 154, and the hub operating portion 160, will be referred to as a "catheter member 168".

As illustrated in FIG. 21, the inner needle 156 is formed sufficiently longer than the catheter 152. In the initial state of the catheter assembly 10C, the needlepoint 157 protrudes from a leading end opening of the catheter 152 by a predetermined length. The inner needle 156 according to the third embodiment is longer than the inner needles 16 and 86 according to the first and second embodiments, respectively.

In the initial state of the catheter assembly 10C, the inner needle 156 has a midway part in the longitudinal direction inserted into the inside of the catheter hub 154, and has the side of the base end held inside the housing 158.

The housing 158 can include a hollow housing main body 170 included in a shell to be gripped by the user, and an inner needle holding portion 101 provided on the base end side of the housing main body 170. The housing main body 170 according to the third embodiment is longer than the housing main body 36 according to the first and second embodiments.

In the initial state of the catheter assembly 10C, the catheter 152 and the inner needle 156 are exposed from the leading end of the housing 158, and the catheter hub 154 and the protector 90 are housed in the housing 158. As a result, the leading end of the housing 158 protrudes to a midway of the catheter 152. According to the present embodiment, a position of the base end of the catheter hub 154 is positioned on the base end side beyond a position of the center in an axial direction of the housing 158, and the leading end of the housing 158 is positioned on the leading end side beyond a position of the center in a longitudinal direction of the catheter 152.

In the initial state of the catheter assembly 10C, most of the hub operating portion 160 is housed in the housing 158, and the leading end portion of the hub operating portion 160 (tab 162) is exposed on the leading end side beyond the leading end of the housing 158.

Figure 26:
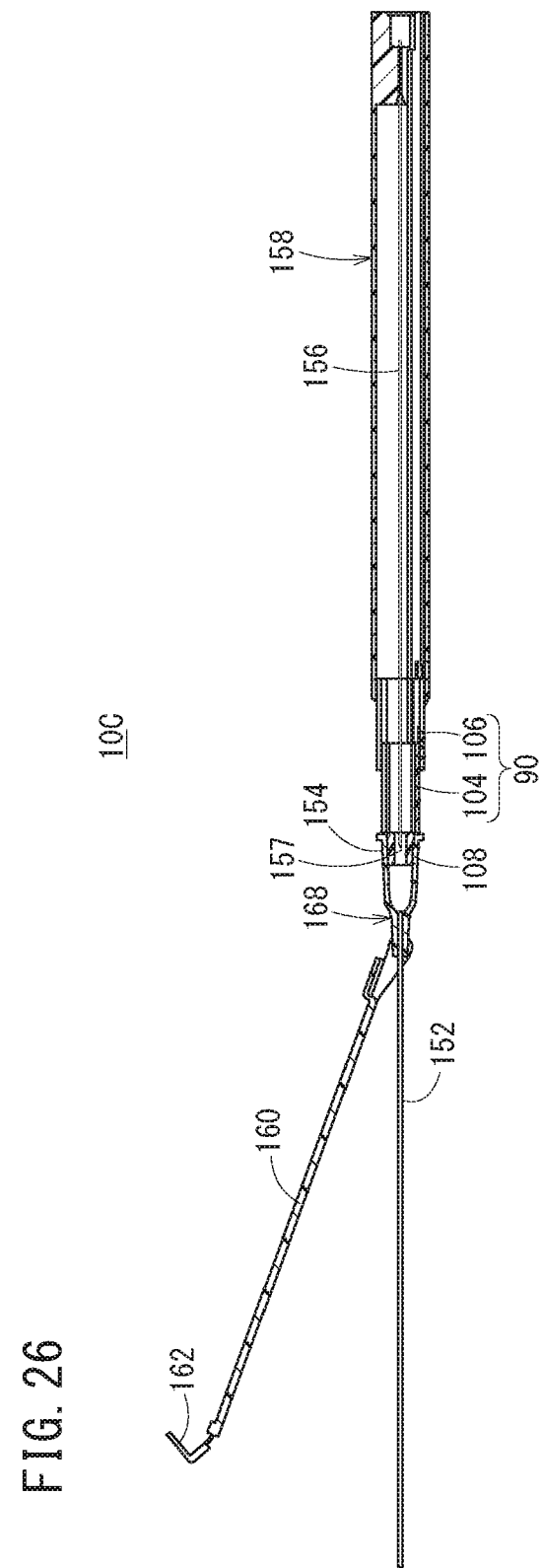
FIG. 26 is a longitudinal-sectional view of a state where the hub operating portion has further moved forward from the state of FIG. 25 and a protector has maximally extended.

The protector 90 houses the inner needle 156 upon evulsion of the inner needle 156 from the catheter 152 so as to cover the needlepoint 157 of the inner needle 156. The protector 90 according to the third embodiment has a configuration similar to that of the protector 90 according to the second embodiment, and has an inner tube 104 and an outer tube 106. In the initial state, a leading end fitting portion 108 of the inner tube 104 fits to the inside of the base end of the catheter hub 154. Upon an evulsion operation of the inner needle 156 from the catheter 152, the protector 90 extends with the housing 158 so as to cover an entire length of the inner needle 156 (refer to FIG. 26). Note that the catheter assembly 10C also can include the first locking mechanism 126 and the second locking mechanism 134 illustrated in FIG. 15.

As illustrated in FIGS. 19 to 21, the catheter assembly 10C further can include a needle support portion 172 in order to inhibit deflection of the inner needle 156 upon a puncture. The needle support portion 172 supports the inner needle 156 through a catheter 152 on the leading end side beyond the catheter hub 154 in the initial state. The needle support portion 172 is provided movable with respect to the housing 158 in order to change from a first state of supporting the inner needle 156 to a second state of releasing the support with respect to the inner needle 156 and allowing the catheter hub 154 to pass.

According to the third embodiment, specifically, the needle support portion 172 has a pair of support arms 173 openable and closeable and a restraining portion 176 capable of restraining the pair of support arms 173 in a closed state and also releasing the restraint.

The pair of support arms 173 is rotatably coupled to the housing 158 through a pair of support pins 141. In the present illustrated example, each of the pair of support pins 141 has an axis in an upper and lower direction. The pair of support arms 173 supported by the pair of support pins 141 is openable and closeable in a left and right direction. One of the support arms 173 has a bending engaging groove 174a provided thereon and the other has a bending engaging groove 174b provided thereon when viewed from the front side in the closed state. Each of the engaging grooves 174a and 174b passes through each of the support arms 173 in a longitudinal direction.

In the present illustrated example, the one engaging groove 174a (hereinafter, referred to as a "first engaging groove 174a") and the other engaging groove 174b (hereinafter, referred to as a "second engaging groove 174b) both bend downward. Note that the first engaging groove 174a and the second engaging groove 174b both may bend upward. Alternatively, one may bend upward and the other may bend downward.

A configuration of the pair of support arms 173 according to the third embodiment is similar to the pair of support arms 138 according to the second embodiment except the first engaging groove 174a and the second engaging groove 174b. A coupling structure between the pair of support arms 173 and the housing 158 according to the third embodiment is substantially the same as a coupling structure between the pair of support arms 138 and the housing 88 according to the second embodiment.

The restraining portion 176 is slidable with respect to the pair of support arms 173, and is formed as a part of the above hub operating portion 160. The restraining portion 176 moves forward in accordance with a forward movement of the hub operating portion 160 so that the restraint with respect to the pair of support arms 173 is released.

Figure 23:
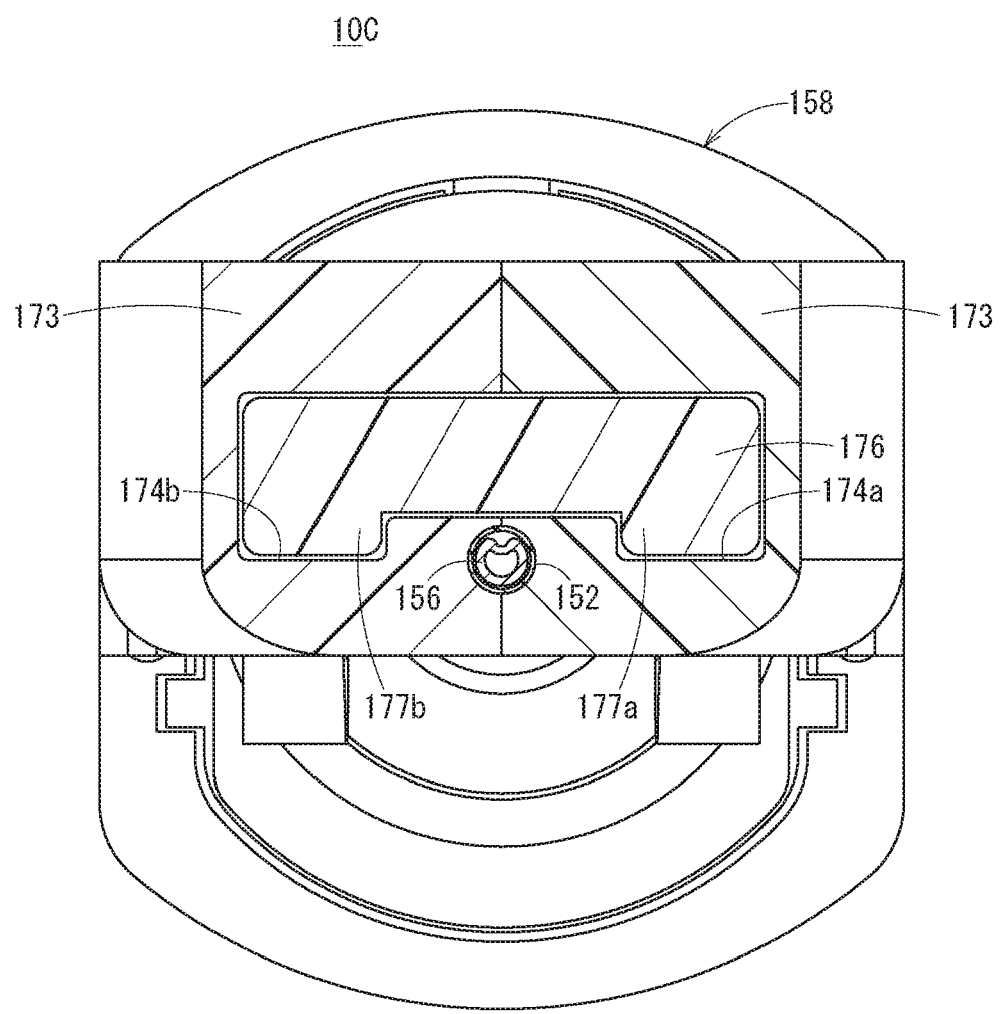
FIG. 23 is a cross-sectional view taken along line XXIII-XXIII of FIG. 21.

Specifically, the restraining portion 176 is provided at a leading end of the main body portion 161 of the hub operating portion 160. FIG. 23 is a cross-sectional view taken along line XXIII-XXIII of FIG. 21. As illustrated in FIG. 23, the restraining portion 176 has a first restraining protrusion 177a engaging with the first engaging groove 174a so as to be slidable and a second restraining protrusion 177b engaging with the second engaging groove 174b so as to be slidable.

In the present illustrated example, the first restraining protrusion 177a and the second restraining protrusion 177b protrude in the same direction so as to adapt to shapes of the first engaging groove 174a and the second engaging groove 174b provided on the pair of support arms 173, respectively. When the restraining portion 176 is positioned at an initial position (backward position), the first restraining protrusion 177a and the second restraining protrusion 177b of the restraining portion 176 engage with the first engaging groove 174a and the second engaging groove 174b of the pair of support arms 173, respectively. Thus, the pair of support arms 173 is restrained in a closed state.

In accordance with a movement of the restraining portion 176 in the leading end direction, the first restraining protrusion 177a and the second restraining protrusion 177b separate from the first engaging groove 174a and the second engaging groove 174b of the pair of support arms 173 in the leading end direction, respectively. When the first restraining protrusion 177a and the second restraining protrusion 177b separate from the first engaging groove 174a and the second engaging groove 174b, respectively, the restraint of the restraining portion 176 with respect to the pair of support arms 173 is released. Then, the pair of support arms 173 becomes expansible.

As illustrated in FIGS. 19 and 20, the hub operating portion 160 can include a protrusion for expansion 178 for opening the pair of support arms 173, provided slightly on the base end side beyond the restraining portion 176. The protrusion for expansion 178 is formed so as to be tapered and be triangular in the present illustrated example.

Note that the respective members in the catheter assembly 10C according to the third embodiment, having the same terms as those in the catheter assemblies 10A and 10B according to the first and second embodiments include the materials exemplified as constituent materials of those of the catheter assemblies 10A and 10B.

The catheter assembly 10C according to the third embodiment is basically constituted as described above. Functions and effects of the catheter assembly 10C will be described below.

As illustrated in FIGS. 19 and 21, the catheter assembly 10C in the initial state is in a state to be described below. The inner needle 156 has been inserted into the catheter 152 and the needlepoint 157 has protruded from the leading end of the catheter 152 by the predetermined length. The leading end fitting portion 108 of the inner tube 104 has been inserted into the base end of the catheter hub 154. The outer tube 106 has maximally moved to the leading end side in a movable range with respect to the inner tube 104. The catheter 152 and the inner needle 156 have been exposed from the leading end of the housing 158, and the catheter hub 154 and the protector 90 have been housed in the housing 158. The protector 90 is positioned on the base end side in the housing 158. The restraining portion 176 has been positioned at the backward position in a movable range. The pair of support arms 173 has been restrained in the closed state by the restraining portion 176. The inner needle 156 has been held by the pair of support arms 173 in the closed state through the catheter 152.

In the use of the catheter assembly 10C, a user (for example, a medical doctor or a nurse) grips the housing 158 and punctures a blood vessel of a patient with the catheter 152 and the inner needle 156. In this case, a portion close to the leading end of the housing 158 is gripped so that the needlepoint 157 becomes stable and the puncture operation is easily performed. Upon the puncture, the pair of support arms 173 that has been closed supports the inner needle 156 through the catheter 152. Thus, the deflection of the inner needle 156 upon the puncture is inhibited. Accordingly, a stable puncture can be performed.

After the puncture, a finger hooks the tab 162 provided at a leading end of the hub operating portion 160, and presses the tab 162 in the leading end direction. In this case, a finger of a hand (for example, an index finger) that has gripped the part close to the leading end of the housing 158, can operate the tab 162. Thus, transition from the operation of the puncture to the operation of the tab 162, is promptly performed.

When the tab 162 is pressed in the leading end portion, the restraining portion 176 provided on the hub operating portion 160 moves in the leading end direction with respect to the pair of support arms 173. Then, the first restraining protrusion 177a and the second restraining protrusion 177b separate from the first engaging groove 174a and the second engaging groove 174b, respectively. Due to the separation, the restraint of the restraining portion 176 with respect to the pair of support arms 173 is released. Then, the pair of support arms 173 becomes expansible.

Figure 24A:
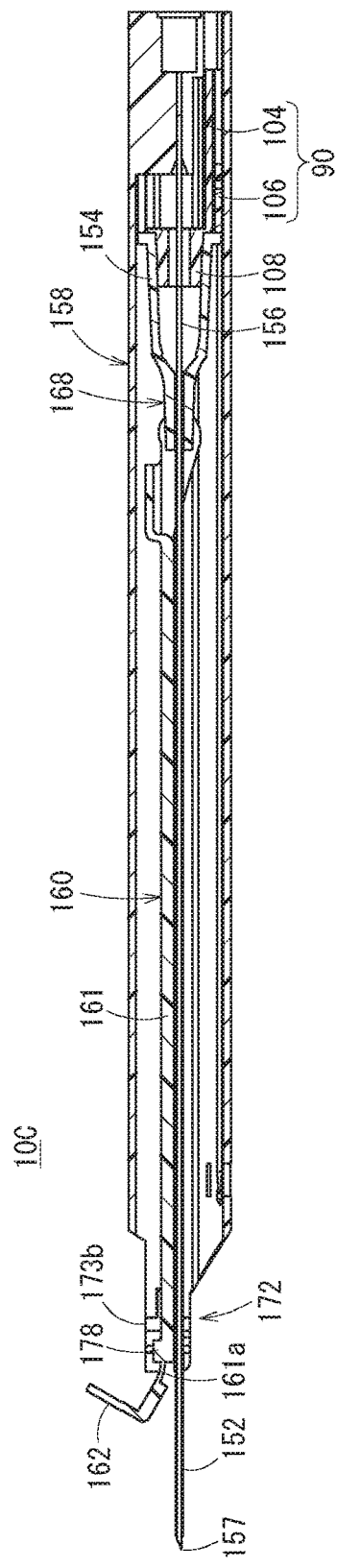
FIG. 24A is a longitudinal-sectional view of the catheter assembly illustrated in FIG. 19 in a state where the hub operating portion has moved forward and slightly.
Figure 24B:
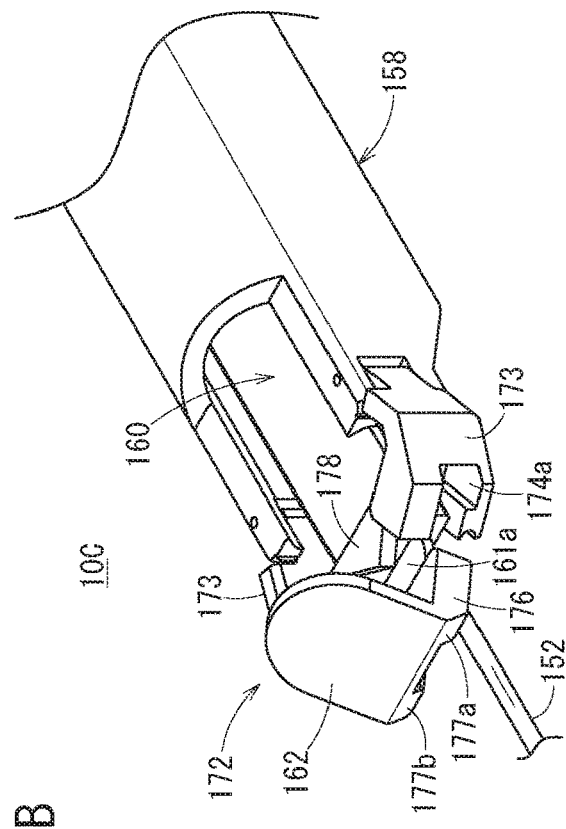
FIG. 24B is a perspective view of a part of the catheter assembly in the state of FIG. 24A.

As illustrated in FIGS. 24A and 24B, when the hub operating portion 160 further moves forward, the pair of support arms 173 is pressed from the rear side by the protrusion for expansion 178 so as to expand. In this case, the leading end portion of the hub operating portion 160 is flexible at a part of a thin-walled portion 161a. Thus, the leading end of the hub operating portion 160 can be prevented from interfering with skin of the patient.

Figure 25:
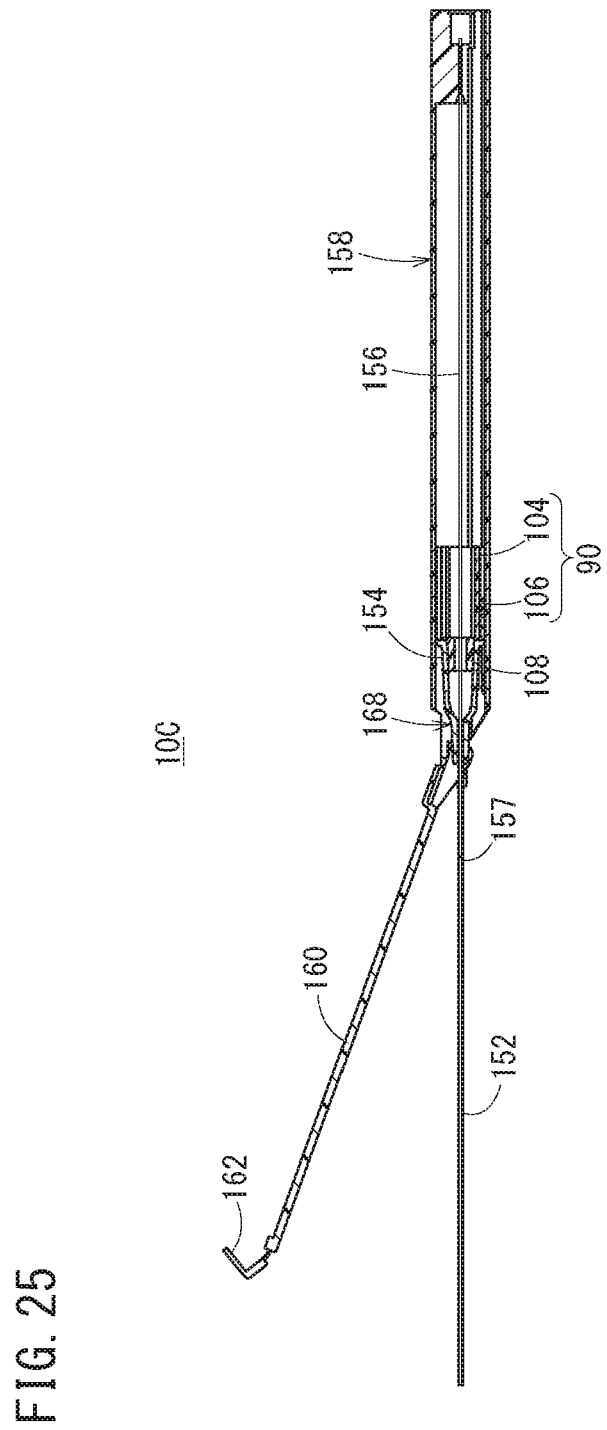
FIG. 25 is a longitudinal-sectional view of a state where the hub operating portion has further moved forward from the state of FIG. 24A.

Next, as illustrated in FIG. 25, when the hub operating portion 160 further moves forward, the catheter hub 154 and catheter 152 that have been coupled to the hub operating portion 160 further move in the leading end direction with respect to the housing 158. Thus, an insertion length of the catheter 152 into the blood vessel increases. Meanwhile, the protector 90 coupled to the catheter hub 154 also moves forward in the housing 158 in accordance with the forward movement of the hub operating portion 160.

When the catheter 152 has been inserted into the blood vessel by a predetermined length, next, the housing 158 is pulled in the base end direction with respect to the catheter member 168. Accordingly, the inner needle 156 moves in the base end direction in the catheter 152, the catheter hub 154, and the protector 90. In this case, since the leading end fitting portion 108 of the inner tube 104 of the protector 90 and the catheter hub 154 have fitted to each other due to predetermined fitting force, the protector 90 extends in accordance with the backward movement of the housing 158. Specifically, the inner tube 104 moves to the side of a leading end of the outer tube 106. In addition, the outer tube 106 moves to the side of the leading end of the housing 158. Accordingly, a state where the protector 90 has maximally extended, is acquired (refer to FIG. 26). During a process during which the protector 90 maximally extends, the inner needle 156 is evulsed from the catheter 152 and the inner needle 156 is also housed in the protector 90 with the needlepoint 157.

In a state where the protector 90 has maximally extended, a function of the first locking mechanism 126 prevents movements in the axial direction of the inner tube 104 and the outer tube 106. In addition, a function of the second locking mechanism 134 prevents movements in the axial direction of the outer tube 106 and the housing 158.

Figure 27:
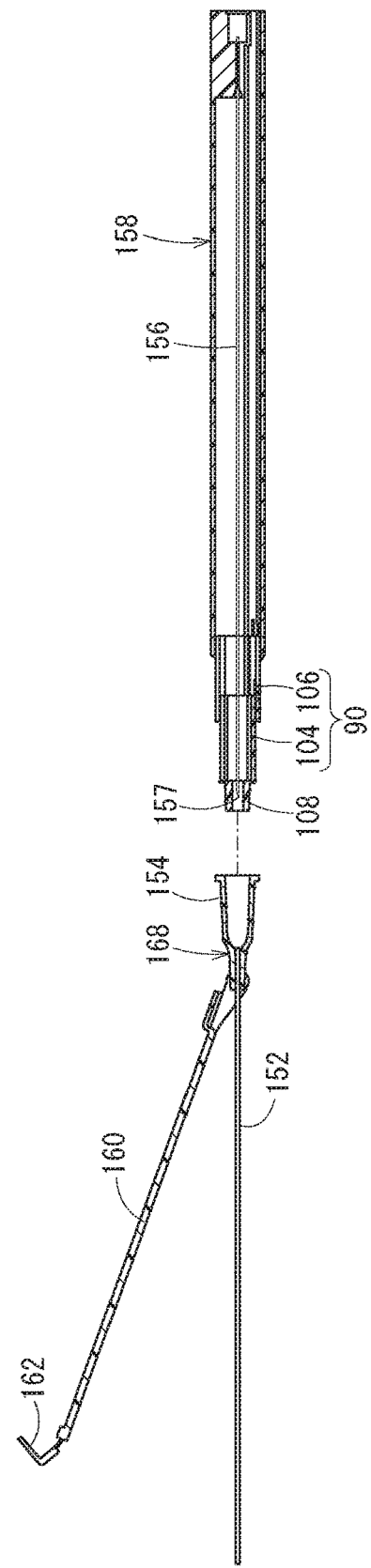
FIG. 27 is a longitudinal-sectional view of the catheter assembly illustrated in FIG. 19 in a state where a catheter member and the protector have separated from each other.

After the protector 90 has maximally extended, when the housing 158 is further pulled in the base end direction with respect to the catheter member 168, as illustrated in FIG. 27, the fit between the catheter hub 154 and the leading end fitting portion 108 of the inner tube 104 comes off. Accordingly, a state where the protector 90 has completely separated from the catheter member 168 and only the catheter member 168 out of the catheter assembly 10C has been detained on the side of the patient, is acquired.

After the catheter member 168 and the protector 90 have separated from each other, the hub operating portion 160 separates from the catheter hub 154. Specifically, in a state where the hub operating portion 160 has risen so as to be in a position substantially perpendicular to the catheter hub 154, the hub operating portion 160 is pulled upward so that the hub operating portion 160 separates from the catheter hub 154 (refer to FIG. 22B). After that, the catheter hub 154 is fixed to the skin of the patient with a dressing material, a tape, or the like. A connector of a transfusion tube, not illustrated, is coupled to the side of the base end of the catheter hub 154, and supply of a transfusion material (a medical fluid) to the patient through the transfusion tube is performed.

As described above, the catheter assembly 10C according to the third embodiment can include the catheter hub 154 housed in the housing 158 in the initial state. Thus, as in the first and second embodiments, an entire product length can be shortened in both of the initial state and the needlepoint protecting state due to the protector 90. According to the third embodiment, other respective constituent portions shared with the first and second embodiments acquire functions and effects similar to those according to the first and second embodiments.

According to the third embodiment, in the initial state, the hub operating portion 160 extends along the inner needle 156 and the catheter hub 154. In addition, the base end portion is coupled to the catheter hub 154 and the leading end portion is exposed on the side of the leading end of the housing 158. With this configuration, a portion of the hub operating portion 160 that has been exposed on the side of the leading end of the housing 158 is touched so that the operation with respect to the hub operating portion 160 can be performed. Thus, the same hand that grips the side of the leading end of the housing 158 upon a puncture, can operate the hub operating portion 160. Accordingly, the same hand can perform the puncture operation and the forward movement operation of the catheter 152. Thus, excellent operability can be acquired.

According to the third embodiment, the restraining portion 176 is provided as a part of the hub operating portion 160, and the restraint with respect to the pair of support arms 173 is released upon the forward movement of the hub operating portion 160. With this configuration, the restraint with respect to the pair of support arms 173 is automatically released in response to the forward movement of the catheter hub 154 based on the operation with respect to the hub operating portion 160. Thus, there is no need for an independent release operation, and excellent operability can be acquired.

The catheter assembly 10C may further include a guide wire G inserted into the inner needle 156, and a guide wire operating portion 150 for operating the guide wire G, the guide wire operating portion 150 being coupled to the guide wire G (refer to FIG. 21). In this case, the restraining portion 176 may be provided as a part of the guide wire operating portion 150. In accordance with a forward movement of the guide wire operating portion 150, the guide wire operating portion 150 may press the restraining portion 176 so that the restraint with respect to the pair of support arms 173 may be released.

The detailed description above describes a catheter assembly. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:
1. A catheter assembly comprising:
a catheter;
a catheter hub fixed to a base end portion of the catheter;
an inner needle having a needlepoint, and inserted into the catheter so as to be separable;
a housing coupled to the inner needle;
a protector displaceable in an axial direction in a range regulated with respect to the housing, and configured to cover at least the needlepoint of the inner needle in accordance with evulsion of the inner needle from the catheter;
wherein, in an initial state, the catheter and the inner needle are exposed from a leading end of the housing, and the catheter hub and the protector are housed in the housing;
a needle support portion configured to support the inner needle through the catheter on a leading end side beyond the catheter hub;
the needle support portion being movable with respect to the housing in order to change from a first state of supporting the inner needle to a second state of releasing the support of the inner needle and allowing the catheter hub to pass; and
wherein the needle support portion has a pair of support arms openable and closeable, and a restraining portion capable of restraining the pair of support arms in a closed state and releasing a restraint of the pair of support arms.

2. The catheter assembly according to claim 1, comprising:
a locking mechanism preventing displacement of the protector with respect to the housing in a state where the protector has covered the needlepoint;
a passage formed of a groove or a hole extending in the axial direction, being provided on a wall portion included in the housing; and
the locking mechanism has an engaging portion protruding in the passage, and an engaging protrusion provided to the protector and capable of engaging with the engaging portion.

3. The catheter assembly according to claim 2, wherein a coming-off prevention protrusion for preventing the engaging protrusion from coming off into the housing is provided on the engaging protrusion.

4. The catheter assembly according to claim 1, wherein an operating portion for operating the catheter hub is provided on the catheter hub; and
in the initial state, at least a part of the operating portion is exposed from the housing.

5. The catheter assembly according to claim 4, a slit extending in the axial direction and open on a leading end side of the housing, is provided on the housing; and
at least the part of the operating portion is exposed on an outside of the housing through the slit.

6. The catheter assembly according to claim 5, the slit being configured to be shifted to one side in a left and right direction with respect to a center of the housing.

7. The catheter assembly according to claim 5, wherein the operating portion includes a pair of wings mutually protruding in opposite directions from the catheter hub and having flexibility; and
the pair of wings is folded, overlapped each other, and protrudes from the slit in the initial state, and is expansible in a state of separation from the slit.

8. The catheter assembly according to claim 4, wherein the operating portion has a tab exposed outside the housing, and a coupling portion coupling the tab and the catheter hub; and
the coupling portion has flexibility in order to allow the operating portion to fall to a side of the catheter hub.

9. The catheter assembly according to claim 8, wherein the coupling portion has a pedestal configured to abut on an outer surface of the housing so as to be slidable; and
the tab is provided on the pedestal.

10. The catheter assembly according to claim 4, wherein, in the initial state, the operating portion extends along the inner needle and the catheter hub, a base end portion is coupled to the catheter hub, and a leading end portion is exposed on a leading end side of the housing.

11. A catheter assembly comprising:
a catheter;
a catheter hub fixed to a base end portion of the catheter;
an inner needle having a needlepoint, and inserted into the catheter so as to be separable;
a housing coupled to the inner needle;
a protector displaceable in an axial direction and configured to cover at least the needlepoint of the inner needle in accordance with evulsion of the inner needle from the catheter;
a needle support portion configured to support the inner needle through the catheter on a leading end side beyond the catheter hub;
the needle support portion being movable with respect to the housing in order to change from a first state of supporting the inner needle to a second state of releasing the support of the inner needle and allowing the catheter hub to pass;
the needle support portion having a pair of support arms openable and closeable; and
a restraining portion capable of restraining the pair of support arms in a closed state and releasing the restraint of the pair of support arms.

12. The catheter assembly according to claim 11, comprising:
a locking mechanism preventing displacement of the protector with respect to the housing in a state where the protector has covered the needlepoint;
wherein a passage formed of a groove or a hole extending in the axial direction, is provided on a wall portion included in the housing; and
the locking mechanism has an engaging portion protruding in the passage, and an engaging protrusion provided to the protector and capable of engaging with the engaging portion.

13. The catheter assembly according to claim 12, comprising:
a coming-off prevention protrusion on the engaging protrusion, the coming-of prevention protrusion configured to prevent the engaging protrusion from coming off into the housing.

14. The catheter assembly according to claim 11, comprising:
an operating portion for operating the catheter hub and which is provided on the catheter hub; and
a slit extending in the axial direction and open on a leading end side of the housing, is provided on the housing, and at least the part of the operating portion is exposed on an outside of the housing through the slit.

15. The catheter assembly according to claim 14, wherein the operating portion has a tab exposed outside the housing; and
a coupling portion coupling the tab and the catheter hub, and the coupling portion has flexibility in order to allow the operating portion to fall to a side of the catheter hub.

16. The catheter assembly according to claim 15, wherein the coupling portion has a pedestal configured to abut on an outer surface of the housing so as to be slidable, and the tab is provided on the pedestal.

17. The catheter assembly according to claim 14, wherein the operating portion includes a pair of wings mutually protruding in opposite directions from the catheter hub and having flexibility; and
wherein the pair of wings is configured to be folded and overlap each other, and protrude from the slit in an initial state, and is expansible in a state of separation from the slit.

18. A catheter assembly comprising:
a catheter;
a catheter hub fixed to a base end portion of the catheter;
an inner needle having a needlepoint, and inserted into the catheter so as to be separable;
a housing coupled to the inner needle;
a protector displaceable in an axial direction in a range regulated with respect to the housing, configured to cover at least the needlepoint of the inner needle in accordance with evulsion of the inner needle from the catheter; and a needle support portion configured to support the inner needle through the catheter on a leading end side beyond the catheter hub, wherein the needle support portion is movable with respect to the housing in order to change from a first state of supporting the inner needle to a second state of releasing the support of the inner needle and allowing the catheter hub to pass, and the needle support portion having a support arm openable and closeable, and a restraining portion capable of restraining the support arm in a closed state and releasing a restraint of the support arm.

* * * * *